(12) United States Patent
Feinberg et al.

(10) Patent No.: US 12,100,485 B2
(45) Date of Patent: Sep. 24, 2024

(54) MACHINE LEARNING AND MOLECULAR SIMULATION BASED METHODS FOR ENHANCING BINDING AND ACTIVITY PREDICTION

(71) Applicant: The Board of Trustees of the Leland Stanford Junior University, Stanford, CA (US)

(72) Inventors: Evan Nathaniel Feinberg, Fairfield, CT (US); Vijay Satyanand Pande, Los Altos Hills, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 978 days.

(21) Appl. No.: 16/293,607

(22) Filed: Mar. 5, 2019

(65) Prior Publication Data
US 2019/0272887 A1    Sep. 5, 2019

Related U.S. Application Data

(60) Provisional application No. 62/638,805, filed on Mar. 5, 2018.

(51) Int. Cl.
*G16B 5/00*    (2019.01)
*G06F 30/20*    (2020.01)
(Continued)

(52) U.S. Cl.
CPC ............... *G16B 5/00* (2019.02); *G06F 30/20* (2020.01); *G06N 20/20* (2019.01); *G06F 2111/08* (2020.01)

(58) Field of Classification Search
CPC .......... G16B 5/00; G06N 20/20; G06F 30/20; G06F 2111/00
See application file for complete search history.

(56) References Cited

U.S. PATENT DOCUMENTS

| 6,128,606 A | 10/2000 | Bengio et al. |
| 8,874,432 B2 | 10/2014 | Qi et al. |
| (Continued) | | |

FOREIGN PATENT DOCUMENTS

| CN | 104936982 A | * 9/2015 | ......... A01K 67/0278 |
| CN | 107729717 A | * 2/2018 | ............... G16B 5/00 |
| (Continued) | | | |

OTHER PUBLICATIONS

H. Li et al.; "Prediction of estrogen receptor agonists and characterization of associated molecular descriptors by statistical learning methods"; Journal of Molecular Graphics and Modelling 25 (2006) 313-323 (Year: 2006).*

(Continued)

*Primary Examiner* — Jay Hann
*Assistant Examiner* — Nupur Debnath
(74) *Attorney, Agent, or Firm* — KPPB LLP

(57) ABSTRACT

Systems and methods for molecular simulation in accordance with embodiments of the invention are illustrated. One embodiment includes a method for predicting a relationship between a ligand and a receptor. The method includes steps for identifying a plurality of conformations of a receptor, computing docking scores for each of the plurality of conformations and a set of one or more ligands, and predicting a relationship between the set of one or more ligands and the plurality of conformations of the receptor.

20 Claims, 12 Drawing Sheets
(9 of 12 Drawing Sheet(s) Filed in Color)

(51) Int. Cl.
  G06F 111/08 (2020.01)
  G06N 20/20 (2019.01)

(56) References Cited

U.S. PATENT DOCUMENTS

| | | | | |
|---|---|---|---|---|
| 8,949,157 | B2* | 2/2015 | Okuno | G16B 35/00 706/12 |
| 9,373,059 | B1 | 6/2016 | Heifets et al. | |
| 10,696,964 | B2* | 6/2020 | Zhang | G16B 35/00 |
| 10,923,214 | B2 | 2/2021 | Fan et al. | |
| 11,205,113 | B2 | 12/2021 | Riley et al. | |
| 11,727,282 | B2 | 8/2023 | Feinberg et al. | |
| 2002/0072587 | A1* | 6/2002 | Somers | C07K 14/70567 530/350 |
| 2002/0099506 | A1 | 7/2002 | Floriano et al. | |
| 2003/0215877 | A1 | 11/2003 | Love et al. | |
| 2004/0248801 | A1* | 12/2004 | Kiessling | G01N 33/5005 435/7.1 |
| 2005/0053999 | A1* | 3/2005 | Gough | C40B 30/04 435/6.16 |
| 2005/0055187 | A1* | 3/2005 | Sherman | G16C 20/90 703/11 |
| 2007/0134662 | A1 | 6/2007 | Singh et al. | |
| 2007/0196869 | A1* | 8/2007 | Perez | G01N 33/5094 435/7.2 |
| 2009/0037136 | A1* | 2/2009 | Young | G16C 20/50 702/179 |
| 2015/0134315 | A1 | 5/2015 | Sarmiento et al. | |
| 2015/0178442 | A1 | 6/2015 | Abel et al. | |
| 2015/0193575 | A1 | 7/2015 | Houghton et al. | |
| 2015/0355200 | A1 | 12/2015 | Ring et al. | |
| 2016/0300127 | A1 | 10/2016 | Heifets et al. | |
| 2016/0350474 | A1 | 12/2016 | Zheng et al. | |
| 2017/0061276 | A1 | 3/2017 | Riley et al. | |
| 2018/0141958 | A1* | 5/2018 | Morikis | A61K 31/165 |
| 2018/0341754 | A1 | 11/2018 | Fan et al. | |
| 2019/0050538 | A1* | 2/2019 | Luo | G16H 50/20 |
| 2019/0139622 | A1 | 5/2019 | Osthege | |
| 2019/0272468 | A1 | 9/2019 | Feinberg et al. | |
| 2019/0354689 | A1 | 11/2019 | Li et al. | |
| 2020/0176077 | A1* | 6/2020 | Telenti | G16B 20/20 |
| 2023/0281465 | A1 | 9/2023 | Feinberg et al. | |

FOREIGN PATENT DOCUMENTS

| | | |
|---|---|---|
| CN | 112204402 A | 1/2021 |
| CN | 112533941 A | 3/2021 |
| EP | 3762405 | 1/2021 |
| EP | 3762730 | 1/2021 |
| HK | 40038934 A | 7/2021 |
| HK | 40039264 A | 7/2021 |
| HK | 40043309 A | 9/2021 |
| JP | 2005517630 A | 6/2005 |
| JP | 2016166159 A | 9/2016 |
| JP | 2021515233 A | 6/2021 |
| JP | 2021515234 A | 6/2021 |
| JP | 7343911 B2 | 9/2023 |
| KR | 10-2020-0128710 A | 11/2020 |
| KR | 10-2020-0129130 A | 11/2020 |
| WO | 02101077 A2 | 12/2002 |
| WO | 2002101077 A2 | 12/2002 |
| WO | WO-2015081166 A1 * | 6/2015 ............. A61P 25/28 |
| WO | 2017070160 A1 | 4/2017 |
| WO | WO-2017070718 A1 * | 4/2017 ............. A61P 35/00 |
| WO | 2017192872 A1 | 11/2017 |
| WO | 2019099573 A1 | 5/2019 |
| WO | 2019173401 A1 | 9/2019 |
| WO | 2019173407 A1 | 9/2019 |

OTHER PUBLICATIONS

John B. O. Mitchell; "Machine learning methods in chemoinformatics"; vol. 4, Sep./Oct. 2014 (Year: 2014).*
David Zilian et al.; "SFCscoreRF: A Random Forest-Based Scoring Function for Improved Affinity Prediction of Protein-Ligand Complexes"; Journal of Chemical Information and Modeling (Year: 2013).*
Ryan G. Coleman; "Ligand Pose and Orientational Sampling in Molecular Docking"; Oct. 2013 | vol. 8 | Issue 10 (Year: 2013).*
Diwakar Shukla et al.; "Elucidating Ligand-Modulated Conformational Landscape of GPCRs Using Cloud-Computing Approaches"; Methods in Enzymology, vol. 557; 2014 (Year: 2014).*
Michiel J. M. Niesen et al.; "The Role of Conformational Ensembles in Ligand Recognition in G-Protein Coupled Receptors" ; J. Am. Chem. Soc. 2011, 133, 13197-13204 (Year: 2011).*
Brian E. Krumm et al.; "Structure and dynamics of a constitutively active neurotensin receptor"; Scientific Reports | 6:38564 (Year: 2016).*
Hossam M. Ashtawy; "Data-Driven and Task-Specific Scoring Functions for Predicting Ligand Binding Poses and Affinity and for Screening Enrichment"; Dissertation Submitted to Michigan State University (Year: 2017).*
Pedro J. Ballester; "A machine learning approach to predicting protein-ligand binding affinity with applications to molecular docking"; Advance Access publication Mar. 17, 2010 (Year: 2010).*
Qurrat Ul Ain et al.; "Machine-learning scoring functions to improve structure-based binding affinity prediction and virtual screening"; Comput Mol Sci 2015, 5:405-424 (Year: 2015).*
Gabriela S. Heck et al. "Supervised Machine Learning Methods Applied to Predict Ligand Binding Affinity"; Current Medicinal Chemistry, 2017, 24, 1-12 (Year: 2017).*
Qinyi Zhao et al.; "Conformation, structure, and thermodynamics integrative mechanism related to receptor regulation"; Integrative Molecular Medicine (Year: 2017).*
International Search Report and Written Opinion for International Application No. PCT/US2019/020837, completed Jun. 10, 2019, Mailed Jul. 10, 2019, 14 pgs.
International Search Report and Written Opinion for International Application No. PCT/US2019/020843, completed May 2, 2019, Mailed May 17, 2019, 13 pgs.
Invitation to Pay Add'l Fees and Partial Search Rpt Rcvd for International Application PCT/US2019/020837, Mailed May 2, 2019, 3 pgs.
Coley et al., "Convolutional Embedding of Attributed Molecular Graphs for Physical Property Prediction", Journal of Chemical Information and Modeling, 2007, vol. 57, No. 8, pp. 1757-1772, http://dx.doi.org/10.1021/acs.jcim.6b00601.
Doerr et al., S., "Dimensionality reduction methods for molecular simulations", arXiv preprint arXiv:1710.10629, Oct. 29, 2017, pp. 1-11.
Feinberg, Evan N., "Molecular Dynamics with Spatial Graph Convolutions", A Whitepaper and Project Proposal, Program in Biophysics, Stanford University, pp. 1-6.
Feinberg et al., "PotentialNet for Molecular Property Prediction", ACS Central Science, Nov. 2, 2018, vol. 4, pp. 1520-1530.
Feinberg et al., Evan N., "Spatial Graph Convolutions for Drug Discovery", ArXiv preprint arXiv:1803.04465, 2018, pp. 1-15.
Feinberg et al., Evan, "Machine Learning Harnesses Molecular Dynamics to Discover New µ Opioid Chemotypes", ArXiv preprint arXiv:1803.04479, Mar. 12, 2018, 6 pgs.
Gilmer et al., "Neural Message Passing for Quantum Chemistry", Proceedings of the 34th International Conference on Machine Learning, Sydney, Australia, PMLR 70, 2017, 14 pgs., arXiv:1704.01212, Jun. 12, 2017.
Gomes et al., "Atomic Convolutional Networks for Predicting Protein-Ligand Binding Affinity", Mar. 30, 2017; Abstract; p. 2 para. 3; Figures 1,2 Tables 1-4; and entire document, pp. 1-17, arXiv:1703.10603.
Hochuli et al., "Visualizing Convolutional Neural Network Protein-Ligand Scoring", Journal of Molecular Graphics and Modeling (preprint), Mar. 8, 2018, pp. 1-11, arXiv:1803.02398, Mar. 6, 2018.
Kearnes et al., "Molecular graph convolutions: moving beyond fingerprints", J. Comp. Aided Mol. Des., 2016, vol. 30, No. 8; pp. 595-608, Author manuscript; available in PMC Aug. 24, 2017, doi:10.1007/s10822-016-9938-8.

(56) References Cited

OTHER PUBLICATIONS

Kitchen et al., "Docking and scoring in virtual screening for drug discovery: methods and applications", Nature Reviews | Drug Discovery, Nov. 2004, vol. 3, pp. 935-949.
Li et al., "Gated Graph Sequence Neural Networks", arXiv preprint arXiv:1511.05493, 2015, pp. 1-20.
McGibbon, Robert T., "Identification of simple reaction coordinates from complex dynamics", The Journal of Chemical Physics, vol. 146, No. 4, 2017, 18 pgs., arXiv:1602.08776, Jan. 6, 2017.
Wu et al., "MoleculeNet: a benchmark for molecular machine learning", Chemical Science, 2018, vol. 9, pp. 513-530, DOI:10.1039/c7sc02664a.
Zhou, Zhenpeng, "Convolution on Graph: A High-Order and Adaptive Approach", arXiv:1706.09916 (Oct. 20, 2017), 2018, 8 pgs.
Extended European Search Report for European Application No. 19763344.9, Search completed Oct. 22, 2021, Mailed Nov. 2, 2021, 12 Pgs.
Extended European Search Report for European Application No. 19764602.9, Search completed Oct. 22, 2021, Mailed Nov. 2, 2021, 8 Pgs.
International Preliminary Report on Patentability for International Application PCT/US2019/020837, Report issued Sep. 8, 2020, Mailed Sep. 17, 2020, 10 Pgs.
International Preliminary Report on Patentability for International Application PCT/US2019/020843, Report issued Sep. 8, 2020, Mailed Sep. 17, 2020, 5 Pgs.
Ballester, "Machine Learning Scoring Functions Based on Random Forest and Support Vector Regression," International Conference on Imae Analysis and Processing, 17th International Conference, Nov. 8, 2012, XP047470176, 12 pgs.
Feinberg et al., "Kinetic Machine Learning Unravels Ligand-Directed Conformational Change of μ Opioid Receptor," BioRxiv, Jul. 31, 2017, XP055853266. 18 Pgs.
Li et al., "Adaptive Graph Convolutional Neural Networks," arxiv. org, Cornell University Library, Jan. 10, 2018, XP081205326.
Li et al., "Learning Graph While Training: An Evolving Graph Convolutional Neural Network," Submitted to 31st Conference on Neural Information Processing Systems, Aug. 10, 2017.
Li et al., "Learning Graph-Level Representation for Drug Discovery," arXiv:1709.03741v2 [cs.LG]. Sep. 16, 2017.
Merkwirth et al., "Automatic Generation of Complementary Descriptors with Molecular Graph Networks," J. Chem. Inf. Model, 2005, 45, 1159-1168.
Shang et al., "Edge Attention-Based Multi-Relational Graph Convolutional Networks," arxiv.org, Cornell University Library, Feb. 14, 2018, XP080856627.
Weiner et al., "AMBER: Assisted Model Building with Energy Refinement. A General Program for Modeling Molecules and Their Interactions," Journal of Computational Chemistry, Jan. 14, 1981, vol. 2, No. 3, 287-303.
Rumelhart et al., "Learning representations by back-propagating errors", 1986, Retrieved from the Internet from http://www.cs.utoronto.ca/hinton/absps/naturebp.pdf.
Such et al., "Robust Spatial Filtering with Graph Convolutional Neural Networks", Jul. 14, 2017, Retrieved from the Internet from https://arxiv.org/pdf/1703.00792.pdf.
Zeiler et al., "Stochastic Pooling for Regularization of Deep Convolutional Neural Networks", Jan. 16, 2013, Retrieved from the Internet from https://arxiv.org/pdf/1301.3557.pdf.
Artemenko, "Distance Dependent Scoring Function for Describing Protein-Ligand Intermolecular Interactions", Journal of Chemical Information and Modeling, 2008, vol. 48, No. 3, pp. 569-574.
Ballester et al., "Does a More Precise Chemical Description of Protein-Ligand Complexes Lead to More Accurate Prediction of Binding Affinity?", Journal of Chemical Information and Modeling, 2014, vol. 54, No. 3, pp. 944-955.
Cang et al., "TopologyNet: Topology based deep convolutional and multi-task neural networks for biomolecular property predictions", PLos Computational Biology, 2017, vol. 13, No. 7, pp. 1-27.
Faber et al., "Prediction Errors of Molecular Machine Learning Models Lower than Hybrid DFT Error", Journal of Chemical Theory and Computation, 2017, vol. 13, No. 11, pp. 5255-5264.
Heck et al., "Supervised Machine Learning Methods Applied to Predict Ligand Binding Affinity", Current Medicinal Chemistry, 2017, vol. 24, pp. 2459-2470.
English Translation of Office Action for Japanese Patent Application No. 2020- 546374, Mailed Apr. 3, 2023, 7 pages.
Artemenko, "Distance Dependent Scoring Function for Describing Protein-Ligand Intermolecular Interactions", Journal of Chemical Information and Modeling, 2008, vol. 48(3), pp. 569-574.
Ballester et al., "Does a More Precise Chemical Description of Protein-Ligand Complexes Lead to More Accurate Prediction of Binding Affinity?", Journal of Chemical Information and Modeling, 2014, vol. 54(3), pp. 944-955.
Bortolato et al., "Molecular Docking Methodologies", Biomolecular Simulations. Methods in Molecular Biology, vol. 924 pp. 339-360 (2012).
Cang et al., "TopologyNet: Topology based deep convolutional and multi-task neural networks for biomolecular property predictions", PLos Computational Biology, 2017, vol. 13(7), pp. 1-27.
Desaphy et al., "Encoding Protein-Ligand Interaction Patterns in Fingerprints and Graphs", J. Chem. Inf. Model. 2013, vol. 53 No. 3, pp. 623-627.
Faber et al., "Prediction Errors of Molecular Machine Learning Models Lower than Hybrid DFT Error", Journal of Chemical Theory and Computation, 2017, vol. 13 (11), pp. 5255-5264.
Fout et al., "Protein Interface Prediction using Graph Convolutional Networks", 31st Conference on Neural Information Processing Systems, 2017, vol. 31, pp. 1-10.
Hayatshahi, "The Effect of Atomistic Interactions on Rna Conformational Distributions, Folding and Ligand Binding Via Molecular Dynamics Simulations and Docking", The University of Utah, 2017.
Kearnes et al., "Molecular Graph Convolutions: Moving Beyond Fingerprints", arXiv, 2016, v1603.00856v3, pp. 1-29.
Keil et al., "Pattern Recognition Strategies for Molecular Surfaces: III. Binding Site Prediction with a Neural Network", Journal of Computational Chemistry, 2004, vol. 25(6), pp. 779-789.
Martiny et al., "In Silico Mechanistic Profiling to Probe Small Molecule Binding to Sulfotransferases", PLoS One, 2013, vol. 8, e73587.
Medina et al., "CALI: A Novel Visual Model for Frequent Pattern Mining in Protein-Ligand Graphs", IEEE 17th International Conference on Bioinformatics and Bioengineering (BIBE), (2017), vol. 17, pp. 352-358.
Pereira et al., "Boosting Docking-based Virtual Screening with Deep Learning", arXiv, 2016, v1608.04844v2, pp. 1-18.
Schafer et al., "Computation and Visualization of Protein Topology Graphs Including Ligand Information", German Conference on Bioinformatics, 2012, pp. 108-118.
Xu et al., "An overview of neural networks for drug discovery and the inputs used", Expert Opinion on Drug Discovery, 2018, vol. 13 (12), pp. 1091-1102.
Ng et al., "Competitive Molecular Docking Approach for Predicting Estrogen Receptor Subtype α Agonists and Antagonists", BMC Bioinformatics. 2014; 15(Suppl 11): S4.
Kipf et al., "Semi-Supervised Classification with Graph Convolutional Networks", Published as a conference paper at ICLR 2017, arXiv:1609.02907v4 [cs.LG] Feb. 22, 2017, 14 pgs.

* cited by examiner

| FMP # | Molecular Weight | Structure | FMP # | Molecular Weight | Structure |
|---|---|---|---|---|---|
| 1 | 261.409 |  | 5 | 331.45 |  |
| 2 | 220.272 |  | 6 | 277.408 |  |
| 3 | 298.471 |  | 7 | 284.403 |  |
| 4 | 286.419 |  | 8 | 317.388 |  |

| FMP # | Molecular Weight | Structure |
|---|---|---|
| 9 | 379.43 | 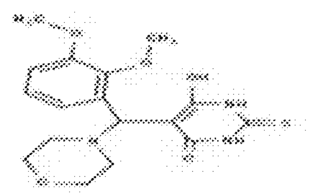 |
| 10 | 347.353 | 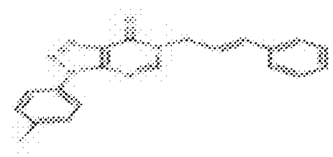 |
| 11 | 255.4 | 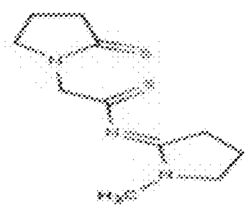 |
| 12 | 249.33 | 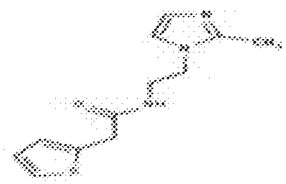 |

| FMP # | Molecular Weight | Structure |
|---|---|---|
| 13 | 228.31 | 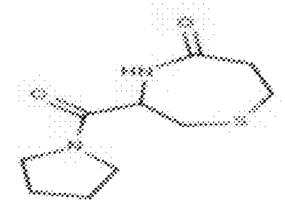 |
| 14 | 325.324 | 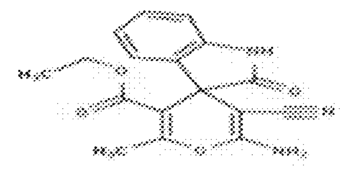 |
| 15 | 207.273 | 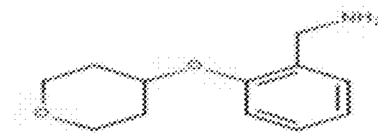 |
| 16 | 286.419 | 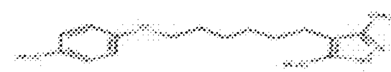 |

FIG. 8B

| FMP # | Molecular Weight | Structure |
|---|---|---|
| 17 | 282.77 | 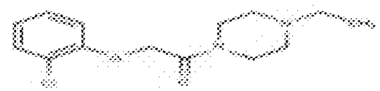 |
| 18 | 335.23 | 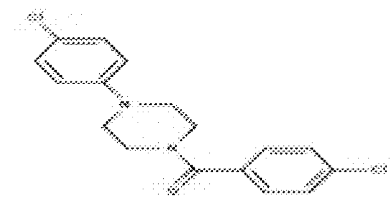 |
| 19 | 265.353 | 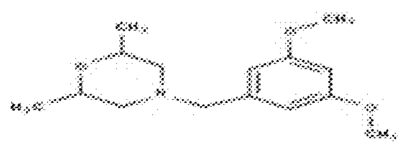 |
| 20 | 291.435 | 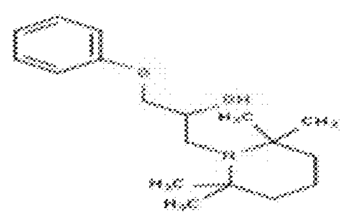 |

| FMP # | Molecular Weight | Structure |
|---|---|---|
| 21 | 290.451 | 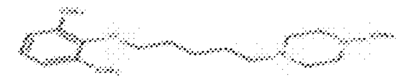 |
| 22 | 308.422 | 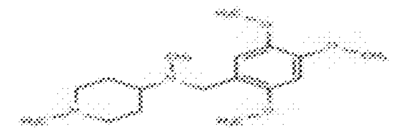 |
| 23 | 354.47 | 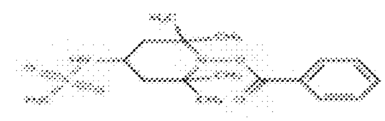 |
| 24 | 408.28 | 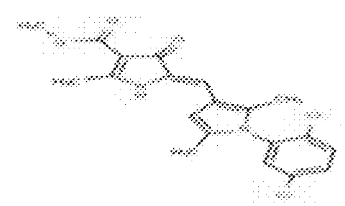 |

| FMP # | Molecular Weight | Structure |
|---|---|---|
| 25 | 390.399 | 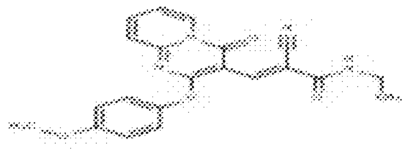 |
| 26 | 309.453 | 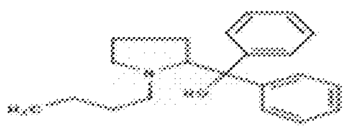 |
| 27 | 253.301 | 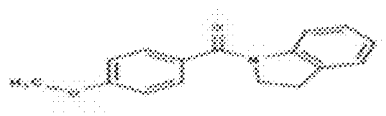 |
| 28 | 343.28 | 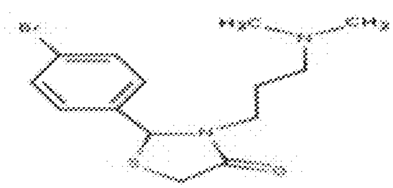 |
| 29 | 285.387 | |
| 30 | 263.381 | |
| 31 | 225 | |
| 32 | 280 | |

FIG. 8D

MACHINE LEARNING AND MOLECULAR SIMULATION BASED METHODS FOR ENHANCING BINDING AND ACTIVITY PREDICTION

CROSS-REFERENCE TO RELATED APPLICATIONS

The current application claims the benefit of and priority under 35 U.S.C. § 119(e) to U.S. Provisional Patent Application No. 62/638,805 entitled "Machine Learning and Molecular Simulation Based Methods for Enhancing Binding and Activity Prediction" filed Mar. 5, 2018. The disclosure of U.S. Provisional Patent Application No. 62/638,805 is hereby incorporated by reference in its entirety for all purposes.

FIELD OF THE INVENTION

The present invention generally relates to machine learning methods and, more specifically, the use of machine learning in molecular simulation.

BACKGROUND

A single class of proteins, the G-Protein Coupled Receptors (GPCRs), comprises over one-third of the targets of all FDA-approved drugs. One such GPCR, the p Opioid Receptor (pOR), epitomizes the benefits and drawbacks of existing GPCR drugs. Opioid chronic pain medications, such as morphine and hydrocodone, are pOR agonists that achieve their main therapeutic aim of analgesia, yet cause severe side effects, such as respiratory depression and addiction.

More than 30,000 Americans died of opioid drug overdose in the year 2015, up from 20,000 only five years earlier. Over the past century, medicinal chemists have striven in vain to synthesize an opioid analgesic without issues of dependence.

SUMMARY OF THE INVENTION

Systems and methods for molecular simulation in accordance with embodiments of the invention are illustrated. One embodiment includes a method for predicting a relationship between a ligand and a receptor. The method includes steps for identifying a plurality of conformations of a receptor, computing docking scores for each of the plurality of conformations and a set of one or more ligands, and predicting a relationship between the set of one or more ligands and the plurality of conformations of the receptor.

In a further embodiment, the plurality of conformations includes at least one non-crystallographic state.

In still another embodiment, identifying the plurality of conformations includes generating simulation data from simulating an interaction of the receptor with a ligand.

In a still further embodiment, identifying the plurality of conformations further includes performing a clustering operation on the simulation data to identify the plurality of conformations.

In yet another embodiment, the clustering operation is a minibatch k-means clustering operation.

In a yet further embodiment, identifying the plurality of conformations further includes performing a dimensionality reduction operation on the simulation data.

In another additional embodiment, identifying the plurality of conformations includes identifying a set of reaction coordinates for each conformation of the plurality of conformations.

In a further additional embodiment, computing the docking scores includes simulating a docking of the set of ligands and each of the plurality of conformations.

In another embodiment again, computing the docking scores includes building a feature matrix of docking scores, wherein predicting the relationship includes inputting the feature matrix into a machine learning model.

In a further embodiment again, the machine learning model includes a random forest model.

In still yet another embodiment, the random forest has a pIC50 cutoff of 8.0 (10 nM).

In a still yet further embodiment, the random forest is a first random forest model, wherein the machine learning model further includes a second random forest model.

In still another additional embodiment, the first random forest model is for binding and the second random forest model is for agonism.

In a still further additional embodiment, the first random forest model and the second random forest model are applied to a library ligand in order to generate a final score from both the first random forest model and the second random forest model respectively.

In still another embodiment again, the method further includes steps for training the machine learning model with ligands from a database of ligands with known pharmacologies.

In a still further embodiment again, predicting the relationship includes determining whether the ligand is an agonist with the receptor.

In yet another additional embodiment, the method further includes steps for identifying a set of one or more candidate ligands based on the predicted relationships, and physically testing reactions of the set of candidate ligands with the receptor.

In a yet further additional embodiment, predicting the relationship comprises predicting a relationship for the set of ligands and each conformation of the plurality of conformations, and predicting an aggregate relationship for the set of ligands and the receptor based on the predicted relationships for the plurality of conformations.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The description and claims will be more fully understood with reference to the following figures and data graphs, which are presented as exemplary embodiments of the invention and should not be construed as a complete recitation of the scope of the invention.

FIGS. 8A-8D illustrate structures and molecular weights for FMP1-FMP32.

DETAILED DESCRIPTION

Figure 1:
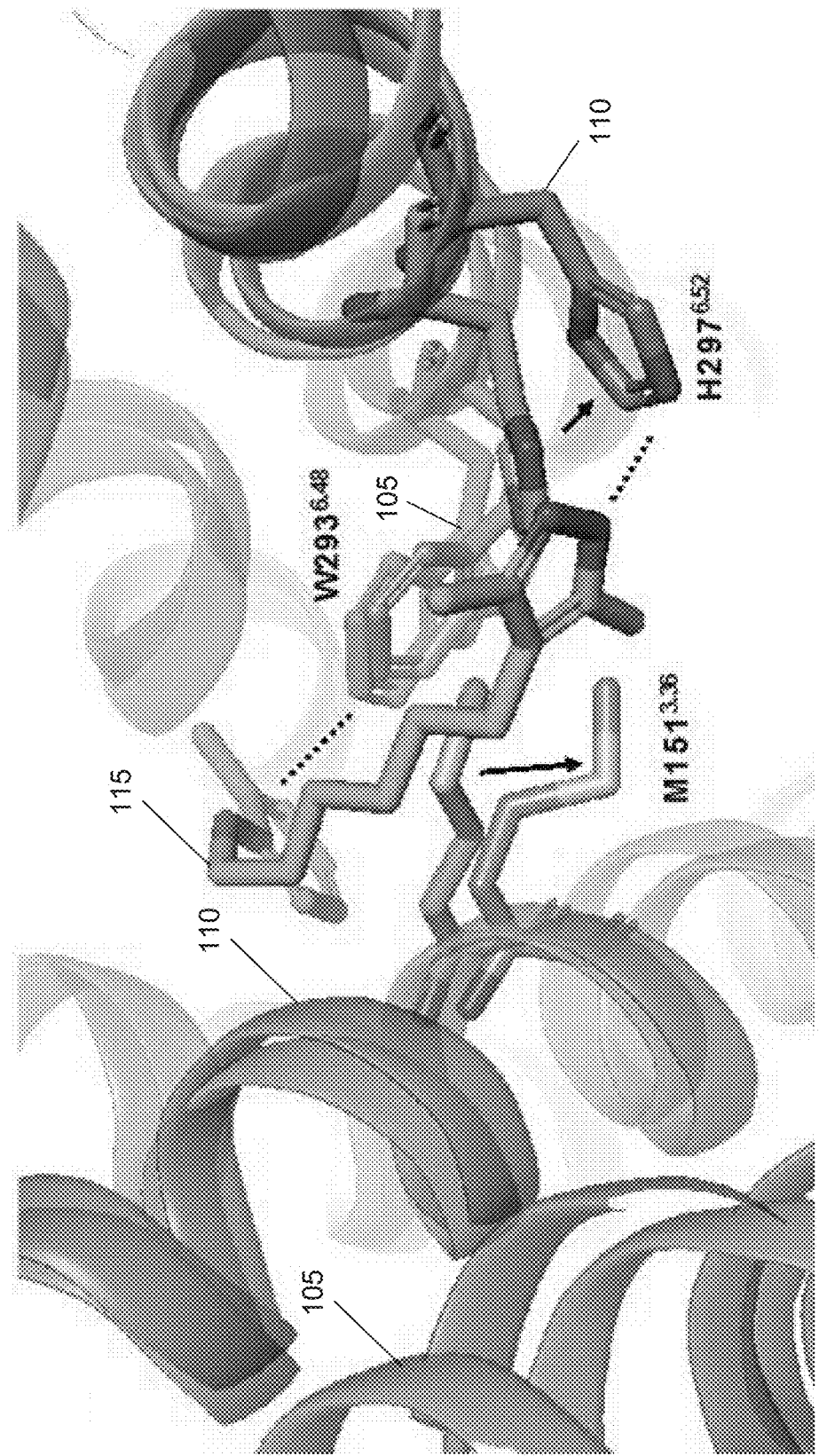
FIG. 1 illustrates an example of various states of pOR.

Systems and methods in accordance with certain embodiments of the invention can assist translational researchers in identifying novel G-Protein Coupled Receptors (GPCR) drug scaffolds. Despite immense efforts in medicinal chemistry on synthesizing derivatives of existing chemotypes, current FDA-approved opioids are riddled with serious side effects that restrict their utility in treating acute and chronic pain. Methods in accordance with several embodiments of the invention leverage crystallography and molecular modeling with machine learning to explore previously uncharted chemical space of molecules active at p Opioid Receptor (pOR). Although many of the examples are described with reference to the pOR, one skilled in the art will readily appreciate that approaches in accordance with several embodiments of the invention can be readily applied to any receptor which is expected to have any sort of conformational plasticity, including other proteins, enzymes, GPCRs, kinases, ion channels, and nuclear receptors.

A significant portion of currently known opioids are analogs of one of two scaffolds: morphine and fentanyl. The vast majority of currently known opioids are centered on a tertiary amine nitrogen motif. Departing from this century-old strategy of creating derivatives, systems and methods in accordance with some embodiments of the invention can be used to open completely new regions of chemical space for development of a novel class of p opioids. In some embodiments, the present disclosure provides system and methods that can be used to develop novel ligands for GPCRs, kinases, ion channels, and nuclear receptors.

Developing fundamentally new molecules demands creative approaches to their discovery. For decades, researchers have used three key methods for drug discovery: structural biology (e.g. crystallography), molecular simulation (e.g. molecular dynamics, docking), and machine learning (e.g. Quantitative Structure-Activity Relationship (QSAR), Random Forests, etc.). However, these methods have been used independently, as there has been no scheme that can synthesize these seemingly orthogonal methods. In some embodiments, a novel process draws on all of these approaches in order to greatly improve our predictive ability in drug design. The success of this scheme supports a key hypothesis in protein function more broadly: protein receptors sample a complex conformational landscape in their functional duties.

Computational chemists typically assay drug candidates by virtually screening compounds against crystal structures of a protein despite the fact that some targets, like the p Opioid Receptor and other members of the GPCR family, traverse many non-crystallographic states. Some embodiments of the invention provide a method for discovering new conformational states of a protein, for example pOR, with molecular dynamics simulation and then using machine learning to learn ligand-structure relationships to predict ligand function. The method in accordance with several embodiments of the invention leverages the conformational plasticity of proteins with machine learning to systematically discover novel active lead molecules. Structure-activity studies using classical medicinal chemistry approaches using these templates as a starting point may lead to compounds with higher affinity at the receptor.

Like other GPCRs, pOR is not a binary switch. Rather, biophysical experiments indicate that GPCRs in general and pOR in particular traverse a spectrum of conformational states. μOR samples a multiplicity of functionally relevant and pharmacologically predictive states. This multiplicity of states is inaccessible to current drug discovery scientists. Processes in accordance with many embodiments of the invention provide novel computational methods that use unprecedented millisecond-scale molecular dynamic simulations to identify and incorporate these states, both yielding an increased AUC in activity prediction and empowering the discovery of new chemical scaffolds. Specifically, in this example, identifying important pOR states beyond the two crystal structures can improve the ability to predict the activity of ligands at the receptor. This method is applicable to other molecules (or a single molecule) of interest that may bind to a receptor.

In some embodiments, a key element of this approach is the estimation of the affinity of each ligand for each of several conformations of a receptor. In contrast to many previous virtual screening approaches, which are predicated solely on ligand-derived features, processes in accordance with some embodiments of the invention are based on the affinities of a given ligand toward each receptor conformation. In certain embodiments, these conformations can be obtained in a single MD simulation pre-step and span a structural basis set for the receptor's functionality. In contrast, induced fit docking samples different conformations to estimate a single docking (affinity) score for the protein. Conformational sampling is spatiotemporally limited, extends only to the binding pocket, must be repeated for each ligand, and, by outputting a single number correlated with affinity it is intrinsically not targeted for predicting agonism.

Long timescale molecular dynamics (MD) simulations of a protein of interest (in this example, pOR) are conducted, either unliganded or bound to one of several ligands. In this example, simulations were conducted bound to one of several agonists: BU72, Sufentanil, TRV130, and IBNtxA. MD simulations in accordance with a number of embodiments of the invention can provide a heterogeneous yet comprehensive spectrum of conformations that the protein (e.g., pOR) can adopt. This dataset expands upon previous works which focus on the conformational dynamics of the receptor. To systematically process a large parallel MD dataset (e.g., consisting of an unprecedented 1.1 milliseconds of pOR simulation), a kinetically motivated machine learning approach in accordance with a number of embodiments can be applied that (1) identifies the most salient reaction coordinates (in this case, the slowest dynamical modes) of the receptor (e.g., pOR) using a variety of methods such as (but not limited to) the cutting-edge Sparse time-structure independent components analysis (tICA) algorithm and (2) defines discrete receptor states using clustering methods, such as (but not limited to) Minibatch K-Means clustering. In some embodiments (1) may utilize Sparse time-structure independent components analysis, time-structure independent components analysis, principal component analysis (PCA), and/or independent component analysis (ICA). In some embodiments (2) may utilize Mini-batch K-Means clustering, K-Means clustering, Stochastic Gradient Descent (SGD) K-Means, k-medoids, gaussian mixture modelling, Jenks natural breaks optimization, Fuzzy C-Means Clustering, k-means++, X-means clustering, G-means clustering, internal cluster evaluation, and/or Minkowski weighted k-means.

In some embodiments, the ligand(s) can be docked when a computational simulation of a candidate ligand binds to a receptor. In some embodiments, binding can be an attractive interaction between two or more molecules that results in a stable association in which the molecules are in close proximity to each other. In some embodiments, binding can be non-covalent. In some embodiments, binding can be reversible covalent. In some embodiments, binding can be irreversible covalent. In some embodiments, binding can involve chemical bonding.

In several embodiments, this unsupervised step uncovers key conformations of pOR, consisting both of intermediates between as well as non-canonical states distinct from the crystal structures. An example of various states of pOR are illustrated in FIG. 1. This figure shows active crystal structure (PDB:5C1M) 105, MD state 3 110, and a docked pose of FMP4 to MD State 3 115. FMP4 is a molecule that was identified through processes in accordance with numerous embodiments of the invention as having an affinity for pOR and is an agonist for the receptor as well. Solid arrows represent changes in MD from crystal structures. Dashed lines indicate non-covalent interactions between FMP4 and pOR binding pocket residues. Note that FMP4 would sterically clash with residues M151 and H297 in the active crystal, possibly accounting for its very low docking score to that structure. Movements of M151 and H297 enable favorable noncovalent ligand-protein interactions in a non-strained conformation of the ligand. Unlike the morphinan phenol, FMP4's phenyl ring engages with key activation residue W293 with a $\pi$-T aromatic interaction.

By enumerating the state space of pOR, one can query conformations of the receptor to motivate rational design with all-atom structural information. An ineluctable flood of data stems from MD, and it is a significant data science challenge to derive actionable knowledge from a vast dataset of simulation alone. One millisecond of MD saved at one frame per nanosecond would contain one million conformations, far too many to be viewed by expert eyes. Rather, by pursuing a kinetically-motivated statistical approach, methods in accordance with many embodiments of the invention made it possible to discover key conformations of the receptor within a tractable scope.

Figure 2:
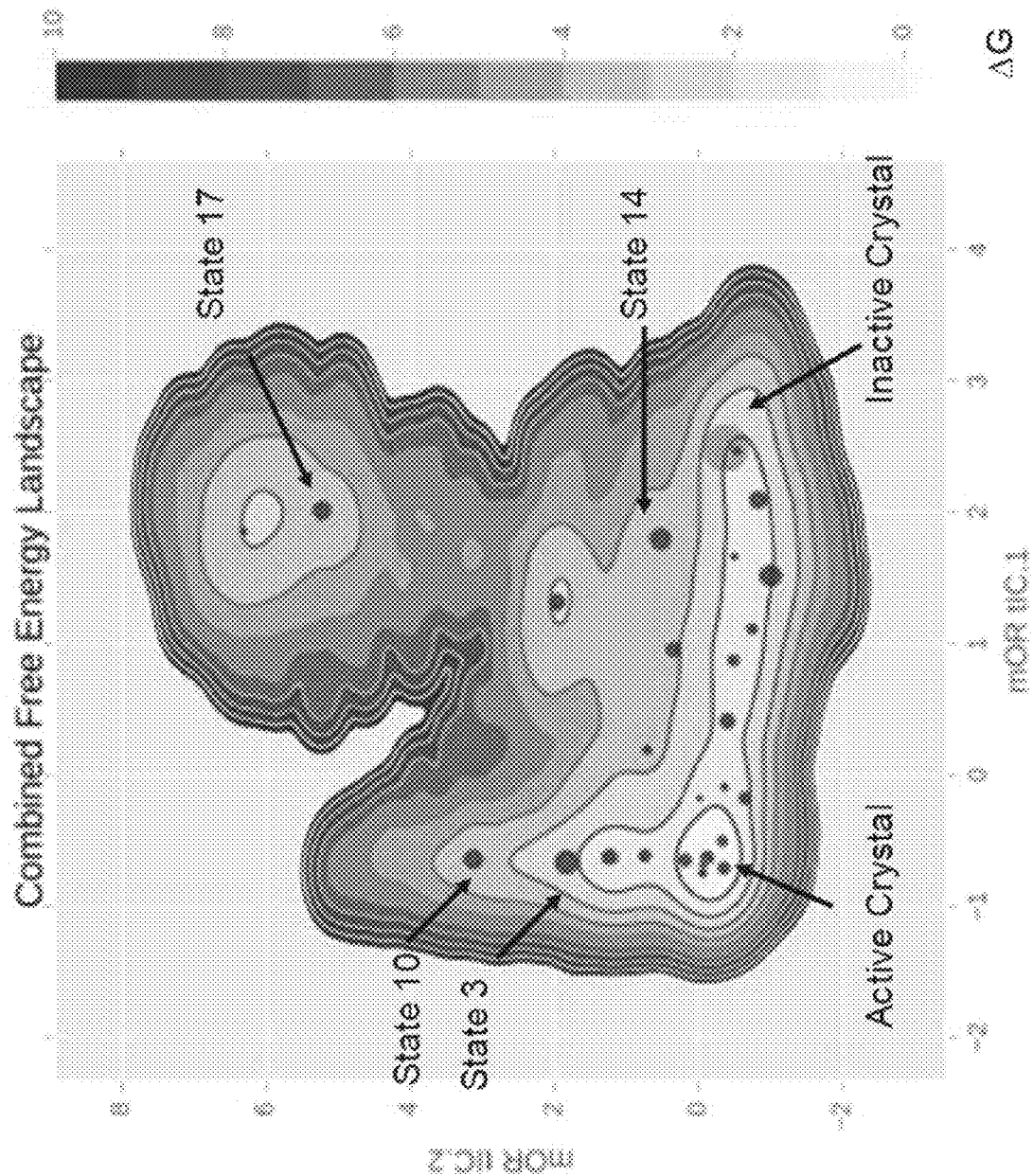
FIG. 2 illustrates a visualization of a free energy landscape of pOR.

A visualization of a free energy landscape of pOR is illustrated in FIG. 2. Specifically, in this example, the free energy landscape of pOR is projected onto its two slowest collective degrees of freedom. Whereas tICA coordinate 1 separates the active and inactive (PDB:4DKL) crystal structures, tICA coordinate 2 is an orthogonal degree of freedom defining several non-crystallographic inactive and active-like states. Such states include State 3, which is critical for FMP4's ability to engage with the receptor.

In light of recent studies, these structures can be potentially druggable states that can be directly employed to enrich rational drug discovery campaigns for pOR. To realize this potential, processes in accordance with some embodiments of the invention train supervised machine learning models to demonstrate significant improvement in two binary classifier tasks: (1) the ability to distinguish agonists from antagonists, and (2) the ability to distinguish binders from non-binders at a receptor.

In some embodiments, random forests are deployed to connect structure to function. One skilled in the art will recognize that other machine learning methods (such as, but not limited to, support vector machines, decision trees, and artificial neural networks) could be employed without departing from the invention. A database of ligands (e.g., opioids) with known pharmacologies can be docked to both the crystal structures as well as to a set of one or more representative conformations of each state. Different conformations in accordance with a variety of embodiments of the invention can include non-crystallographic states or other conformations of a receptor. Conformations in accordance with certain embodiments of the invention can be identified through a variety of methods including (but not limited to) experiments (such as, but not limited to, crystallography, nuclear magnetic resonance (NMR), cryo-electron microscopy (cryoEM), etc.) and/or through computations (such as, but not limited to, molecular dynamics simulation, monte carlo simulations, deep neural network driven conformation generation, etc.).

In certain embodiments, the docking scores of each ligand to each MD conformation can then used as the input, or feature matrix, to binary classifier models for both agonism and binding at a receptor of interest. In a number of embodiments, feature matrices are structures such that each row is a ligand and each column is a feature (docking scores to each of the MD states and to each crystal structure). In various embodiments, entry (i, j) in a feature matrix is the docking score of the i'th ligand to the j'th conformational state. Docking scores may be utilized to determine a rank order with respect to each other i.e., for a set of ligands. Docking scores can correlate a molecule's binding affinity to either a protein as a whole or to a given state of that protein. The matrix can be used for different functions over the docking scores to generate a single number that is a better predictor/correlate of overall affinity. In some embodiments, a priori information of binding affinities or agonisms for N ligands are had, by docking scores for each of the N ligands to each of K conformational states, a function that maps the set of K docking scores to a binding affinity may be obtained.

This dually unsupervised and supervised ML-based synthesis of structural information from both crystallography and MD yields statistically significant enrichment in both tasks. In one example, methods in accordance with some embodiments of the invention—which incorporates docking to the MD states in addition to the crystal structures—achieved a median Area Under the Curve (AUC) improvement in agonism and in binding compared to the crystal structures alone. In some embodiments, the median AUC improvement is about 0.11 in agonism. In some embodiments, the median AUC improvement is from 0.01 to 0.5 in agonism. In some embodiments, the median AUC improvement is from 0.5 to 1.0 in agonism. In some embodiments, the median AUC improvement is from 0.1 to 0.3 in agonism. In some embodiments, the median AUC improvement is from 0.3 to 0.6 in agonism. In some embodiments, the median AUC improvement is from 0.6 to 0.9 in agonism. In some embodiments, the median AUC improvement is about 0.15 in binding. In some embodiments, the median AUC improvement is from 0.01 to 0.5 in binding. In some embodiments, the median AUC improvement is from 0.5 to 1.0 in binding. In some embodiments, the median AUC improvement is from 0.1 to 0.3 in binding. In some embodiments, the median AUC improvement is from 0.3 to 0.6 in binding. In some embodiments, the median AUC improvement is from 0.6 to 0.9 in binding.

As a further test of robustness to agonism, scaffold splits were employed. Specifically, a series of models were trained in which analogs of either methadone or fentanyl were removed from the training data and placed in a held-out test set. In other words, none of these models had any a priori knowledge of methadone (or, alternately, fentanyl) analogs. Nevertheless, the models successfully distinguished both methadone- and fentanyl-derived agonists from random sets of antagonists. Analogous scaffold splits were defined for the binding prediction task, yielding comparable gains in AUC. Therefore, since methods in accordance with many embodiments of the invention do not explicitly incorporate the chemical makeup of the ligand, they can be better equipped to discover new opioid-active scaffolds in addition to derivatives of existing ones. Based on these results, opioid prediction in accordance with a number of embodiments of the invention is enriched by incorporating conformational states that are unforeseeable from crystallography alone and stabilized by ligands in simulation.

Systems and Methods for Ligand Modeling and Prediction

Figure 3:
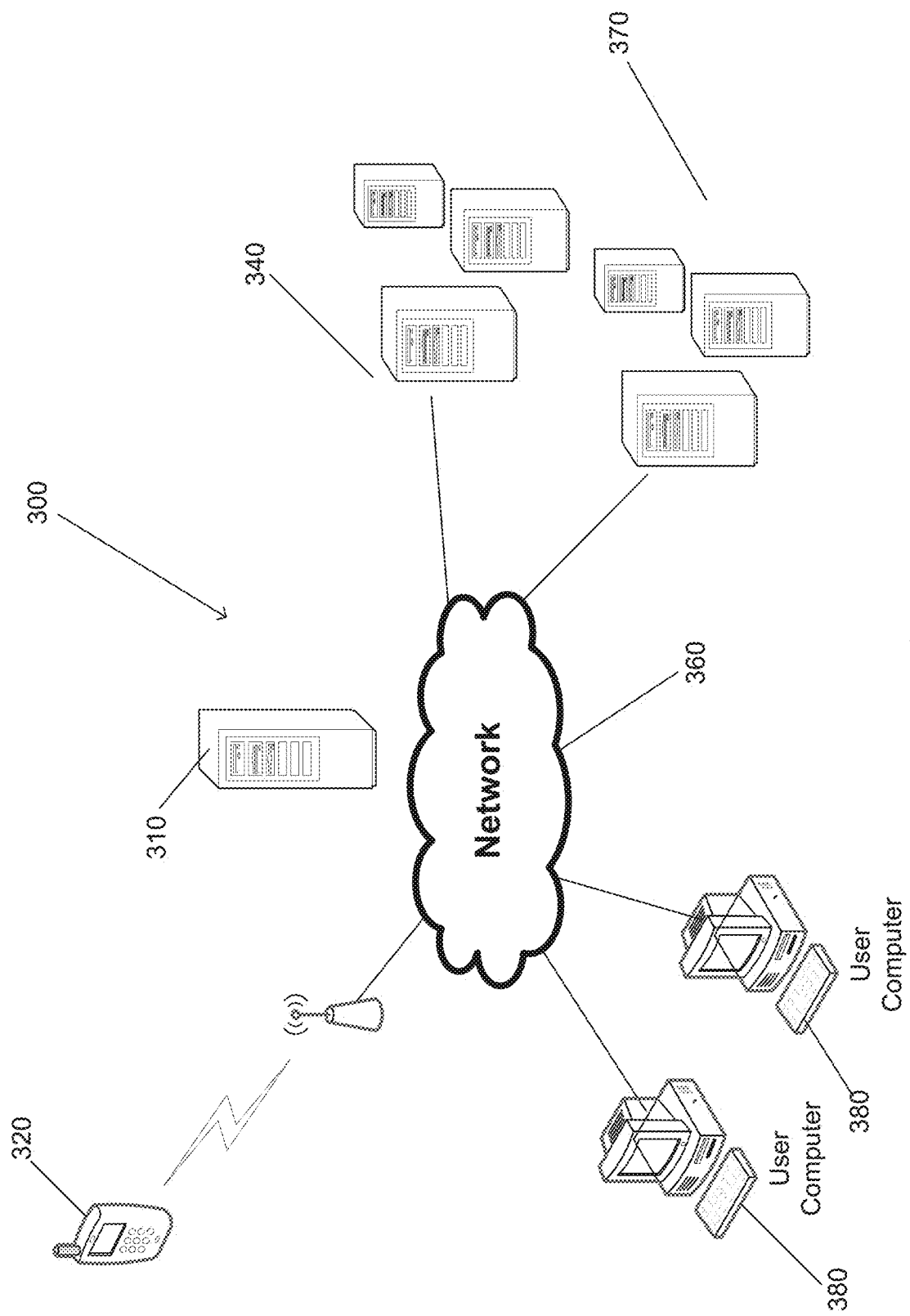
FIG. 3 illustrates an example of a system that provides for ligand discovery in accordance with some embodiments of the invention.

A system that provides for modeling and prediction in accordance with some embodiments of the invention is shown in FIG. 3. Network 300 includes a communications network 360. The communications network 360 is a network such as the Internet that allows devices connected to the network 360 to communicate with other connected devices. Server systems 310, 340, and 370 are connected to the network 360. Each of the server systems 310, 340, and 370 is a group of one or more server computer systems communicatively connected to one another via internal networks that execute processes that provide cloud services to users over the network 360. For purposes of this discussion, cloud services are one or more applications that are executed by one or more server systems to provide data and/or executable applications to devices over a network. The server systems 310, 340, and 370 are shown each having three servers connected via an internal network. However, the server systems 310, 340 and 370 may include any number of servers and any additional number of server systems may be connected to the network 360 to provide cloud services including, but not limited to, virtualized server systems. In accordance with various embodiments of this invention, processes for modeling and predicting ligand properties are provided by one or more software applications executing on a single server system and/or a group of server systems communicating over network 360.

Users may use personal devices 380 and 320 that connect to the network 360 to perform processes for modeling and predicting ligand properties in accordance with various embodiments of the invention. In the illustrated embodiment, the personal devices 380 are shown as desktop computers that are connected via a conventional "wired" connection to the network 360. However, the personal device 380 may be a desktop computer, a laptop computer, a smart television, an entertainment gaming console, or any other device that connects to the network 360 via a "wired" or "wireless" network connection. The mobile device 320 connects to network 360 using a wireless connection. A wireless connection is a connection that uses Radio Frequency (RF) signals, Infrared signals, or any other form of wireless signaling to connect to the network 360. In FIG. 3, the mobile device 320 is a mobile telephone. However, mobile device 320 may be a mobile phone, Personal Digital Assistant (PDA), a tablet, a smartphone, a virtual reality headset, an augmented reality headset, a mixed reality headset or any other type of device that connects to network 360 via wireless connection without departing from this invention. In accordance with some embodiments of the invention, the processes for modeling and predicting ligand properties are performed by the user device.

As can readily be appreciated, the specific computing system used to model and predict ligand properties is largely dependent upon the requirements of a given application and should not be considered as limited to any specific computing system(s) implementation.

Figure 4:
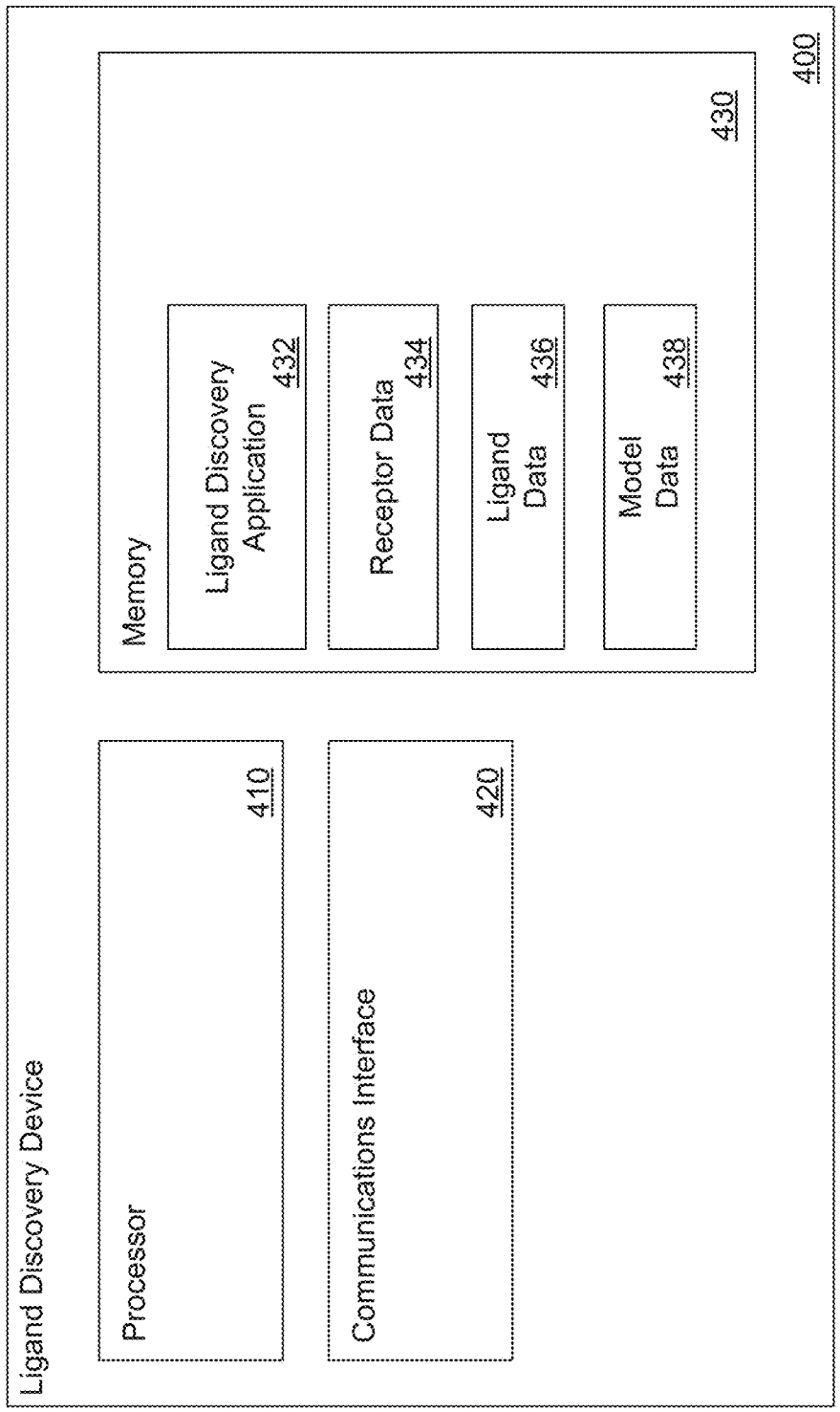
FIG. 4 illustrates an example of a ligand discovery element in accordance with several embodiments of the invention.

A ligand discovery element in accordance with several embodiments of the invention is illustrated in FIG. 4. Ligand discovery elements in accordance with many embodiments of the invention can include (but are not limited to) one or more of mobile devices, computers, servers, and cloud services. Ligand discovery element 400 includes processor 410, communications interface 420, and memory 430.

One skilled in the art will recognize that a particular ligand discovery element may include other components that are omitted for brevity without departing from this invention. The processor 410 can include (but is not limited to) a processor, microprocessor, controller, or a combination of processors, microprocessor, and/or controllers that performs instructions stored in the memory 430 to manipulate data stored in the memory. Processor instructions can configure the processor 410 to perform processes in accordance with certain embodiments of the invention. Communications interface 420 allows training element 400 to transmit and receive data over a network based upon the instructions performed by processor 410.

Memory 430 includes a ligand discovery application 432, receptor data 434, ligand data 436, and model data 438. Ligand discovery applications in accordance with several embodiments of the invention are used to analyze ligands and to identify candidate ligands that can be tested for interactions with a receptor. In several embodiments, ligand discovery applications can use receptor data and/or ligand data that includes data generated from a variety of sources, including (but not limited to) a molecular docking simulation and/or a database of opioids with known pharmacologies. Model data 438 in accordance with various embodiments of the invention can include data for unsupervised and supervised models that can be used for various purposes, such as (but not limited to) clustering to identify discrete conformation states, classifying ligands as an agonist/antagonist, and/or classifying ligands as binding/non-binding.

Although a specific example of a ligand discovery element 400 is illustrated in FIG. 4, any of a variety of training elements can be utilized to perform processes similar to those described herein as appropriate to the requirements of specific applications in accordance with embodiments of the invention.

Figure 5:
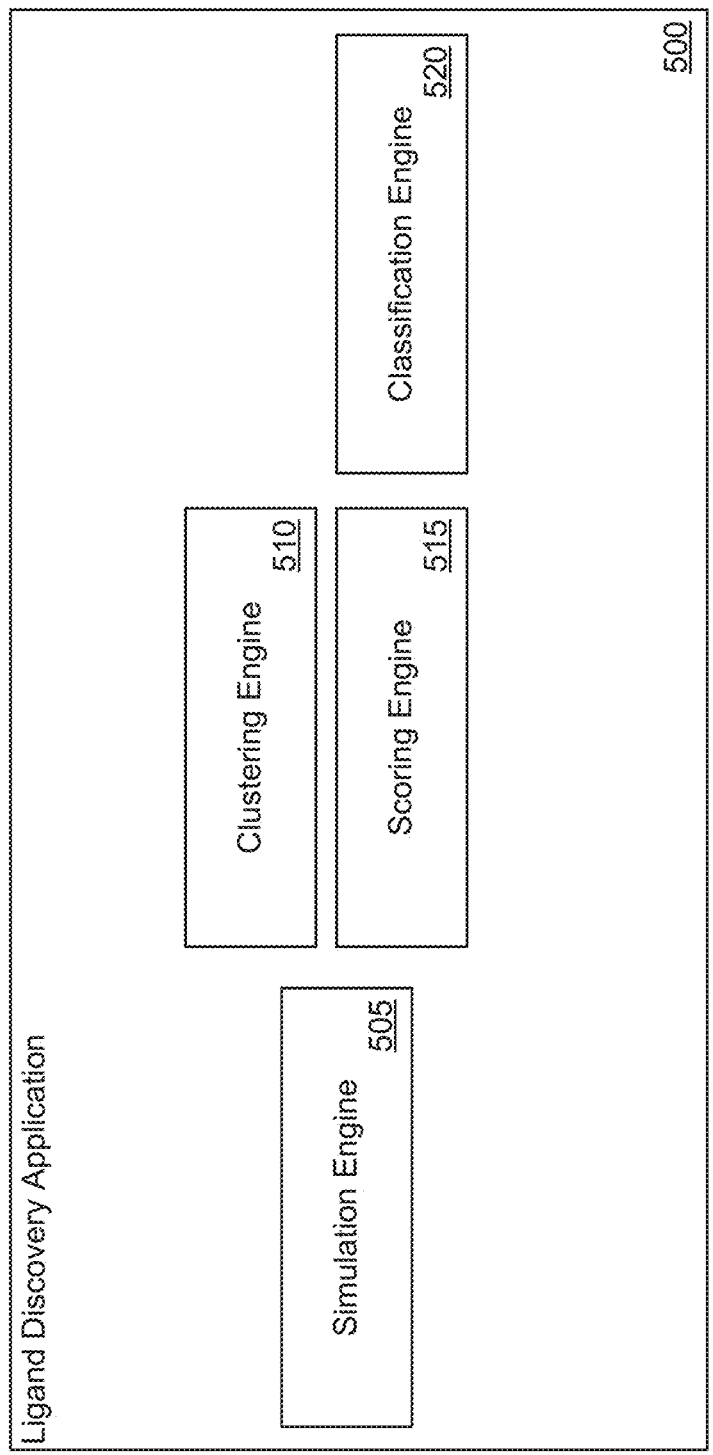
FIG. 5 illustrates an example of a ligand discovery application for identifying candidate ligands in accordance with an embodiment of the invention.

A ligand discovery application for identifying candidate ligands in accordance with an embodiment of the invention is illustrated in FIG. 5. Ligand discovery application 500 includes simulation engine 505, clustering engine 510, scoring engine 515, and classification engine 520. Ligand discovery applications in accordance with many embodiments of the invention can analyze ligand and receptor data to identify candidate ligands for various uses related to a receptor.

In a variety of embodiments, simulation engines can be used to simulate various receptor conformations. In many embodiments, simulation engines can compute docking scores between a ligand and a receptor.

Clustering engines in accordance with numerous embodiments of the invention can identify discrete receptor conformation states based on simulated data. In several embodiments, clustering engines use a clustering process such as (but not limited to minibatch k-means clustering and agglomerative hierarchical clustering.

Scoring engines in accordance with various embodiments of the invention can compute docking scores for ligands with receptors. In numerous embodiments, scoring engines can evaluate simulations of a ligand and a receptor from a simulation engine. Simulations can include simulations of a ligand with several discrete conformations of the receptor identified by a clustering engine. In a number of embodiments, scoring engines can produce a feature matrix of docking scores for a set of ligands and a set of conformation states of the receptor.

In various embodiments, classification engines can be used to classify or predict an interaction between a ligand and a receptor. In some embodiments, the classification engine can be a supervised learning algorithm or an unsupervised learning algorithm, such as (but not limited to) support vector machines, linear regression, logistic regression, naive bayes, linear discriminant analysis, decision tress, k-nearest neighbor algorithm, neural networks, and/or similarity learning. In some embodiments, the supervised learning can be semi-supervised learning, active learning, structure prediction, and/or learning to rank. Classification engines in accordance with some embodiments of the invention can implement a classifier, such as (but not limited to) a fully connected neural network (FCNN) and/or a random forest. In various embodiments, classification engines take as input a feature matrix generated by a scoring engine and output a likelihood that a ligand has a particular relationship (e.g., binding/non-binding, agonist/antagonist, etc.) with a receptor. In some embodiments, a docking score is computed from the product of the two generated final scores by the following equation:

$$P(\text{binder} \cap \text{agonist}|\text{model}) = P(\text{binder}|\text{model}_b) \cdot P(\text{agonist}|\text{model}_a).$$

Although a specific example of a ligand discovery application is illustrated in FIG. 5, any of a variety of ligand discovery applications can be utilized to perform processes similar to those described herein as appropriate to the requirements of specific applications in accordance with embodiments of the invention.

Figure 6:
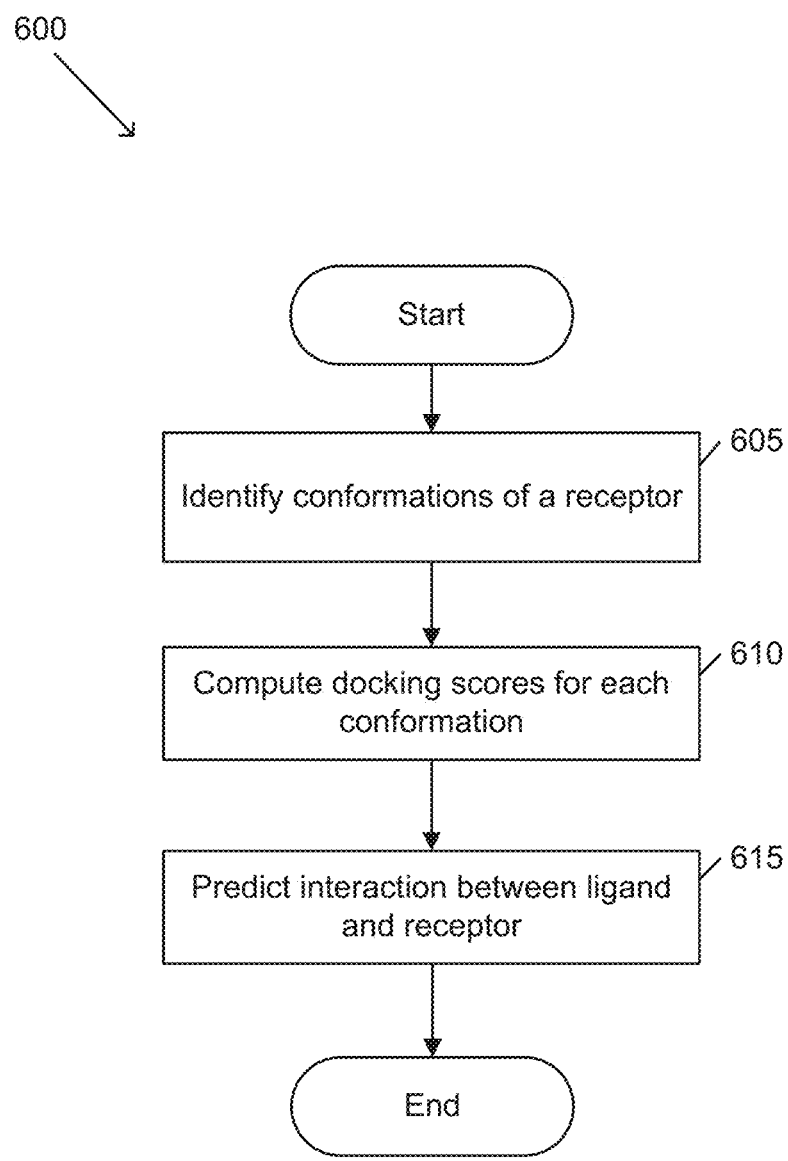
FIG. 6 conceptually illustrates a flowchart of a process for ligand discovery in accordance with an embodiment of the invention.

A flowchart of a process for ligand discovery in accordance with an embodiment of the invention is illustrated in FIG. 6. Process 600 identifies (605) a plurality of conformations of a receptor. In many embodiments, the different conformations (or states) are based on a long timescale molecular docking (MD) simulation of the receptor. Simulations in accordance with several embodiments of the invention can be performed with just the receptor or based on interactions of the receptor with a known ligand. In several embodiments, the different conformations are identified based on a clustering process that identifies clusters in state data generated by a MD simulation. Clustering in accordance with a variety of embodiments of the invention can be performed in a variety of ways, including (but not limited to) Minibatch K-Means clustering and agglomerative hierarchical clustering. The different discrete conformations in accordance with a number of embodiments of the invention can represent various states of the receptor, including (but not limited to) crystal states, intermediates between crystal states, as well as non-canonical states distinct from the crystal structures.

Process 600 computes (610) docking scores for a set of one or more ligands and each conformation of the identified conformations. In a number of embodiments, docking scores can be computed using molecular docking simulations that can simulate the interactions between the set of ligands and each conformation of the receptor. Computed docking scores in accordance with numerous embodiments of the invention can be provided in a feature matrix with a docking score for each ligand-conformation combination.

Process 600 predicts (615) an interaction between the set of ligands and the receptor. In many embodiments, predicted interactions can include whether the set of ligands bind with the receptor. Alternatively, or conjunctively, the predicted interactions can include whether the set of ligands are agonists with the receptor. Predicting the interaction in accordance with many embodiments of the invention can be performed using random forests that are trained to classify a ligand as a binder or agonist with a particular receptor. In certain embodiments, predicting an interaction between a ligand and a receptor includes predicting an interaction between the ligand each conformation of the receptor and then computing an aggregate prediction for the interaction between the ligand and the receptor as a whole. In various embodiments, the predicted interactions are used to identify a set of one or more ligands and physically testing the interactions of the identified ligands with the receptor.

In an aspect, the present disclosure provides a method for predicting a relationship between a ligand and a receptor, the method comprising: identifying a plurality of conformations of a receptor; computing docking scores for each of the plurality of conformations and a set of one or more ligands; and predicting a relationship between the set of one or more ligands and the plurality of conformations of the receptor.

In some embodiments, the plurality of conformations comprises conformations of a single receptor. In some embodiments, the conformations can stem from experiment (crystallography, NMR, CryoEM, etc.) or computation (molecular dynamics simulation, monte carlo simulations, deep neural network driven conformation generation, or a combination thereof.

In some embodiments, the plurality of conformations comprises at least one non-crystallographic state.

In a variety of embodiments, identifying the plurality of conformations comprises generating simulation data from simulating an interaction of the receptor with a ligand.

In several embodiments, identifying the plurality of conformations further comprises performing a clustering operation on the simulation data to identify the plurality of conformations.

In several embodiments, identifying the plurality of conformations further comprises performing a dimensionality reduction operation on the simulation data. The dimensionality reduction operation in accordance with numerous embodiments of the invention can include (but is not limited to) tICA, sparse tICA, ICA, PCA, t-SNE, and others or a combination thereof.

In various embodiments, identifying the plurality of conformations comprises identifying a set of reaction coordinates for each conformation of the plurality of conformations.

In numerous embodiments, computing the docking scores comprises simulating a docking of the set of ligands and each of the plurality of conformations.

In several embodiments, computing the docking scores comprises building a feature matrix of docking scores, wherein predicting the relationship comprises inputting the feature matrix into a machine learning model. In some embodiments, the machine learning model is a random forest.

In numerous embodiments, further training the machine learning model with ligands from a database of ligands with known pharmacologies. In some embodiments, the molecules can be opioids.

Next, predicting the relationship comprises determining whether the ligand is an agonist with the receptor.

Next, identifying a set of one or more candidate ligands based on the predicted relationships; and physically testing reactions of the set of candidate ligands with the receptor.

Next, predicting the relationship comprises: predicting a relationship for the set of ligands and each conformation of the plurality of conformations; and predicting an aggregate relationship for the set of ligands and the receptor based on the predicted relationships for the plurality of conformations.

In some embodiments, the random forest models have a pIC50 cutoff of 8.0 (10 nM). In various embodiments, predicting the relationship comprises predicting a quantitative metric of affinity or agonism, such as (but not limited to) IC50, EC50, and/or Ki. Alternatively, or conjunctively, predicting the relationship in accordance with many embodiments of the invention can comprise classifying the relationship, such as (but not limited to) binder vs. non-binder. In several embodiments, classifying the relationship can be based on some cutoff or threshold value, e.g., pIC50 of 8.0 (10 nM).

Next, further comprising a first random forest model and a second random forest model wherein both models are trained.

Next, wherein the first random forest model is for binding and the second random forest model is for agonism.

Next, wherein the first random forest model and the second random forest model are applied to a library ligand in order to generate a final score from both the first random forest model and the second random forest model respectively.

In another aspect, the present disclosure provides a system for predicting a relationship between a ligand and a receptor, the system comprising: one or more processors that are individually or collectively configured to identify a plurality of conformations of a receptor; compute docking scores for each of the plurality of conformations and a set of one or more ligands; and predict a relationship between the set of one or more ligands and the plurality of conformations of the receptor.

In another aspect, the present disclosure provides methods and systems for drug discovery. The methods may comprise identifying a candidate ligand from predicted molecular characteristics with machine learning. In some embodiments, identifying a candidate ligand comprises: selecting a plurality of conformations of a receptor; computing docking scores for each of the plurality of conformations and a set of one or more ligands; calculating a relationship between the set of one or more ligands and the plurality of conformations of the receptor; and predicting the candidate ligand from the relationship between the set of one or more ligands and the plurality of conformations of the receptor. In some embodiments, the system to identify a candidate ligand comprises the one or more processors that are individually or collectively configured to: select a plurality of conformations of a receptor; compute docking scores for each of the plurality of conformations and a set of one or more ligands; calculate a relationship between the set of one or more ligands and the plurality of conformations of the receptor; and predict the candidate ligand from the relationship between the set of one or more ligands and the plurality of conformations of the receptor.

Specific processes for ligand discovery in accordance with embodiments of the invention are described above; however, one skilled in the art will recognize that any number of processes can be utilized as appropriate to the requirements of specific applications in accordance with embodiments of the invention.

Although the present invention has been described in certain specific aspects, many additional modifications and variations would be apparent to those skilled in the art. It is therefore to be understood that the present invention may be practiced in ways other than specifically described, without departing from the scope and spirit of the present invention. Thus, embodiments of the present invention should be considered in all respects as illustrative and not restrictive.

EXAMPLES

The following examples are offered to illustrate, but not to limit the claimed invention.

Example 1

The following examples are offered to illustrate, but not to limit the claimed invention.

| Name | Action | Name | Action |
|---|---|---|---|
| 7-pet | agonist | bromadoline | agonist |
| acetylfentanyl | agonist | butyrfentanyl | agonist |
| acetylmethadol | agonist | c-8813 | agonist |
| acrylfentanyl | agonist | carfentanil | agonist |
| ah-7921 | agonist | cebranopadol | agonist |
| alfentanil | agonist | chloromorphide | agonist |
| alimadol | agonist | chloroxymorphamine | agonist |
| 3-allylfentanyl | agonist | ciprefadol | agonist |
| allylnorpethidine | agonist | clonitazene | agonist |
| allylprodine | agonist | dadle | agonist |
| alphacetylmethadol | agonist | damgo | agonist |
| alphamethadol | agonist | dermorphin | agonist |
| alphamethylthiofentanyl | agonist | desmethylprodine | agonist |
| anileridine | agonist | desomorphine | agonist |
| azaprocin | agonist | dextromoramide | agonist |
| azidomorphine | agonist | dextropropoxyphene | agonist |
| bdpc | agonist | diampromide | agonist |
| benzethidine | agonist | difenoxin | agonist |

-continued

| Name | Action | Name | Action |
|---|---|---|---|
| betacetylmethadol | agonist | dihydroetorphine | agonist |
| betahydroxyfentanyl | agonist | dihydromorphine | agonist |
| betahydroxythiofentanyl | agonist | dimenoxadol | agonist |
| betamethadol | agonist | dimepheptanol | agonist |
| bezitramide | agonist | dimethylaminopivalophenone | agonist |
| brifentanil | agonist | dioxaphetyl_butyrate | agonist |
| diphenoxylate | agonist | lefetamine | agonist |
| dipipanone | agonist | levacetylmethadol | agonist |
| dpi-3290 | agonist | levallorphan | agonist |
| eluxadoline | agonist | levomethadone | agonist |
| endomorphin | agonist | levophenacylmorphan | agonist |
| endomorphin-1 | agonist | levorphanol | agonist |
| endomorphin-2 | agonist | lofentanil | agonist |
| ethoheptazine | agonist | loperamide | agonist |
| 14-ethoxymetopon | agonist | meprodine | agonist |
| etonitazene | agonist | metethoheptazine | agonist |
| etorphine | agonist | methadone | agonist |
| etoxeridine | agonist | metheptazine | agonist |
| fentanyl | agonist | 4-methoxybutyrfentanyl | agonist |
| 4-fluorobutyrfentanyl | agonist | 14-methoxydihydromorphinone | agonist |
| 4-fluoropethidine | agonist | 14-methoxymetopon | agonist |
| furanylfentanyl | agonist | alpha-methylacetylfentanyl | agonist |
| furethidine | agonist | 3-methylbutyrfentanyl | agonist |
| hemorphin-4 | agonist | n-methylcarfentanil | agonist |
| heterocodeine | agonist | methyldesorphine | agonist |
| hydromorphinol | agonist | methyldihydromorphine | agonist |
| hydromorphone | agonist | 6-methylenedihydrodesoxymorphine | agonist |
| hydroxypethidine | agonist | 3-methylfentanyl | agonist |
| ibntxa | agonist | beta-methylfentanyl | agonist |
| ic-26 | agonist | methylketobemidone | agonist |
| isomethadone | agonist | 3-methylthiofentanyl | agonist |
| ketamine | agonist | metopon | agonist |
| ketobemidone | agonist | mitragynine_pseudoindoxyl | agonist |
| 6-monoacetylmorphine | agonist | phenoperidine | agonist |
| morpheridine | agonist | 4-phenylfentanyl | agonist |
| morphine | agonist | 14-phenylpropoxymetopon | agonist |
| morphine-6-glucuronide | agonist | picenadol | agonist |
| morphinone | agonist | piminodine | agonist |
| mr-2096 | agonist | piritramide | agonist |
| mt-45 | agonist | prodilidine | agonist |
| noracymethadol | agonist | prodine | agonist |
| ocfentanil | agonist | proheptazine | agonist |
| ohmefentanyl | agonist | properidine | agonist |
| oliceridine | agonist | propylketobemidone | agonist |
| oxpheneridine | agonist | prosidol | agonist |
| oxymorphazone | agonist | pzm21 | agonist |
| oxymorphol | agonist | r-4066 | agonist |
| oxymorphone | agonist | r-30490 | agonist |
| parafluorofentanyl | agonist | racemorphan | agonist |
| pentamorphone | agonist | remifentanil | agonist |
| pepap | agonist | ro4-1539 | agonist |
| pethidine | agonist | sc-17599 | agonist |
| phenadoxone | agonist | semorphone | agonist |
| phenampromide | agonist | sufentanil | agonist |
| phenaridine | agonist | thienorphine | agonist |
| phenazocine | agonist | thiofentanyl | agonist |
| pheneridine | agonist | tilidine | agonist |
| n-phenethylnordesomorphine | agonist | trefentanil | agonist |
| n-phenethylnormorphine | agonist | trimeperidine | agonist |
| phenomorphan | agonist | trimu_5 | agonist |
| u-47700 | agonist | bevenopran | antagonist |
| u-77891 | agonist | clocinnamox | antagonist |
| viminol | agonist | cyclofoxy | antagonist |
| 6beta-naltrexol-d4 | antagonist | cyprodime | antagonist |
| beta-chlornaltrexamine | antagonist | eptazocine | antagonist |
| beta-funaltrexamine | antagonist | ly-255582 | antagonist |
| alvimopan | antagonist | methocinnamox | antagonist |
| at-076 | antagonist | methylnaltrexone | antagonist |
| axelopran | antagonist | methylsamidorphan | antagonist |

Example 2

A scaffold split was defined in which (1) agonist ligands with a Tanimoto score of <0.5 compared to fentanyl were placed in a train set, (2) agonist ligands with a Tanimoto score of >0.7 compared to fentanyl were placed in a test set, and (3) antagonists were randomly distributed between the train and test sets.

a)
Fentanyl Analog Ligands (Test Set):
['acetylfentanyl', 'acrylfentanyl', '3-allylfentanyl', 'alphamethylthiofentanyl', 'azaprocin', 'betahydroxyfentanyl', 'betahydroxythiofentanyl', 'butyrfentanyl', 'carfentanil', 'desmethylprodine', 'diampromide', 'fentanyl', '4-fluorobutyrfentanyl', 'furanylfentanyl', 'lofentanil', '4-methoxybutyrfentanyl', 'alpha-methylacetylfentanyl', '3-methylbutyrfentanyl', 'n-methylcarfentanil', '3-methylfentanyl', 'beta-methylfentanyl', '3-methylthiofentanyl', 'ocfentanil', 'ohmefentanyl', 'parafluorofentanyl', 'pepap', 'phenampromide', 'phenaridine', '4-phenylfentanyl', 'prodilidine', 'prodine', 'proheptazine', 'prosidol', 'r-30490', 'remifentanil', 'sufentanil', 'thiofentanyl', 'trimeperidine', 'u-47700']

Non-Fentanyl-Analog Agonists (Train Set):
['7-pet', 'alimadol', 'alphamethadol', 'azidomorphine', 'bdpc', 'betamethadol', 'c-8813', 'cebranopadol', 'chloromorphide', 'chloroxymorphamine', 'ciprefadol', 'clonitazene', 'dadle', 'damgo', 'desomorphine', 'dihydroetorphine', 'dihydromorphine', 'dimenoxadol', 'dimepheptanol', 'dimethylaminopivalophenone', 'eluxadoline', 'endomorphin', 'endomorphin-1', '14-ethoxymetopon', 'etonitazene', 'etorphine', 'hemorphin-4', 'heterocodeine', 'hydromorphinol', 'hydromorphone', 'ibntxa', 'ketamine', 'lefetamine', 'levophenacylmorphan', 'levorphanol', '14-methoxydihydromorphinone', '14-methoxymetopon', 'methyldesorphine', 'methyldihydromorphine', '6-methylenedihydrodesoxymorphine', 'metopon', 'mitragynine_pseudoindoxyl', '6-monoacetylmorphine', 'morphine', 'morphine-6-glucuronide', 'morphinone', 'mr-2096', 'oliceridine', 'oxymorphazone', 'oxymorphol', 'oxymorphone', 'pentamorphone', 'phenazocine', 'n-phenethylnordesomorphine', 'n-phenethylnormorphine', 'phenomorphan', '14-phenylpropoxymetopon', 'picenadol', 'pzm21', 'racemorphan', 'ro4-1539', 'sc-17599', 'semorphone', 'thienorphine', 'tilidine', 'trimu_5', 'viminol']

Antagonists:
['levallorphan', '6beta-naltrexol-d4', 'beta-chlornaltrexamine', 'beta-funaltrexamine', 'alvimopan', 'at-076', 'axelopran', 'bevenopran', 'clocinnamox', 'cyclofoxy', 'cyprodime', 'eptazocine', 'ly-255582', 'methocinnamox', 'methylnaltrexone', 'methylsamidorphan', 'nalmefene', 'naloxazone', 'naloxegol', 'naloxol', 'naloxonazine', 'naloxone', 'naltrexazone', 'naltrexone', 'oxilorphan', 'quadazocine', 'samidorphan']

A scaffold split was defined in which (1) agonist ligands with a Tanimoto score of ≤0.5 compared to methadone were placed in a train set, (2) agonist ligands with a Tanimoto score of ≥0.7 compared to methadone were placed in a test set, and (3) antagonists were randomly distributed between the train and test sets.

b)
Methadone Analog Ligands (Test Set).
['acetylmethadol', 'alphacetylmethadol', 'alphamethadol', 'betacetylmethadol', 'betamethadol', 'dipipanone', 'ic-26', 'isomethadone', 'ketobemidone', 'levacetylmethadol', 'levomethadone', 'methadone', 'methylketobemidone', 'noracymethadol', 'phenadoxone', 'propylketobemidone', 'r4066']

Non-Methadone Analogs (Train Set).
['7-pet', 'alimadol', 'azidomorphine', 'bdpc', 'c-8813', 'cebranopadol', 'chloromorphide', 'chloroxymorphamine', 'ciprefadol', 'clonitazene', 'dadle', 'damgo', 'desomorphine', 'dihydroetorphine', 'dihydromorphine', 'dimenoxadol', 'dimepheptanol', 'dimethylaminopivalophenone', 'eluxadoline', 'endomorphin', 'endomorphin-1', '14-ethoxymetopon', 'etonitazene', 'etorphine', 'hemorphin-4', 'heterocodeine', 'hydromorphinol', 'hydromorphone', 'ibntxa', 'ketamine', 'lefetamine', 'levophenacylmorphan', 'levorphanol', '14-methoxydihydromorphinone', '14-methoxymetopon', 'methyldesorphine', 'methyldihydromorphine', '6-methylenedihydrodesoxymorphine', 'metopon', 'mitragynine_pseudoindoxyl', '6-monoacetylmorphine', 'morphine', 'morphine-6-glucuronide', 'morphinone', 'mr-2096', 'oliceridine', 'oxymorphazone', 'oxymorphol', 'oxymorphone', 'pentamorphone', 'phenazocine', 'n-phenethylnordesomorphine', 'n-phenethylnormorphine', 'phenomorphan', '14-phenylpropoxymetopon', 'picenadol', 'pzm21', 'racemorphan', 'ro4-1539', 'sc-17599', 'semorphone', 'thienorphine', 'tilidine', 'trimu_5', 'viminol']

Antagonists:
['levallorphan', '6beta-naltrexol-d4', 'beta-chlornaltrexamine', 'beta-funaltrexamine', 'alvimopan', 'at-076', 'axelopran', 'bevenopran', 'clocinnamox', 'cyclofoxy', 'cyprodime', 'eptazocine', 'ly-255582', 'methocinnamox', 'methylnaltrexone', 'methylsamidorphan', 'nalmefene', 'naloxazone', 'naloxegol', 'naloxol', 'naloxonazine', 'naloxone', 'naltrexazone', 'naltrexone', 'oxilorphan', 'quadazocine', 'samidorphan']

Example 3

Random Forest average Gini impurity reduction ("importance") of each feature (MD State, Crystal Structure) for a) distinguishing between opioid agonists and antagonists and b) distinguishing between binders and non-binders from µOR.

| a) | | | |
|---|---|---|---|
| Inactive Crystal | 0.063488 | Active Crystal | 0.01358 |
| State 14 | 0.033463 | State 12 | 0.013346 |
| State 3 | 0.031175 | State 6 | 0.012534 |
| State 17 | 0.02995 | State 2 | 0.012306 |
| State 10 | 0.029853 | State 1 | 0.012289 |
| State 23 | 0.025154 | State 20 | 0.01123 |
| State 5 | 0.024361 | | |
| State 16 | 0.023912 | | |
| State 21 | 0.023884 | | |
| State 4 | 0.021384 | | |
| State 22 | 0.020618 | | |
| State 0 | 0.019934 | | |
| State 13 | 0.01972 | | |
| State 18 | 0.017975 | | |
| State 7 | 0.017955 | | |
| State 24 | 0.017434 | | |
| State 11 | 0.017295 | | |
| State 9 | 0.01617 | | |

-continued a)

| | |
|---|---|
| State 8 | 0.015486 |
| State 15 | 0.015193 |
| State 19 | 0.013673 | b)

| | | | |
|---|---|---|---|
| Inactive Crystal | 0.057546 | Active Crystal | 0.01358 |
| State 18 | 0.033463 | State 20 | 0.039999 |
| State 2 | 0.031175 | State 3 | 0.037063 |
| State 14 | 0.02995 | State 24 | 0.035946 |
| State 1 | 0.029853 | State 19 | 0.035883 |
| | | State 17 | 0.035723 |
| | | State 5 | 0.035547 |
| | | State 22 | 0.034922 |
| | | State 16 | 0.034121 |
| | | State 0 | 0.034035 |
| | | State 21 | 0.033999 |
| | | State 4 | 0.033884 |
| | | State 6 | 0.033837 |
| | | State 13 | 0.033381 |
| | | State 10 | 0.032723 |
| | | State 11 | 0.032537 |
| | | State 23 | 0.032248 |
| | | State 12 | 0.032069 |
| | | State 9 | 0.031896 |
| | | State 15 | 0.031409 |
| | | State 8 | 0.030558 |
| | | State 7 | 0.030245 |

Example 4

Docking to both MD states and crystal structures statistically significantly improves ability over crystals alone to distinguish μOR binders from non-binders. Table below shows median ROC Area Under the Curve (AUC) performance over the validation set over 1,000 train-valid splits for different split and model types. Differences between crystal lone and crystal+MD structures methods are considered statistically significant if the lower bound of a 99% Wilson scoring confidence interval (CI) is greater than 0.5. Note that, for each dataset, incorporating MD-derived structures in addition to the crystal structures confers a statistically significant improvement in ability to distinguish binders from non-binder as measured by AUC. Notably, when fentanyl (or methadone) analogs are removed from the training set, models remain able to distinguish fentanyl (or methadone) derivative agonists from random sets of antagonists. This indicates that models fit in this way have the capacity to discover new opioid agonist scaffolds in addition to derivatives of existing ones.

| Dataset | Cross validation split type | AUC (cyrstals alone) | AUC (Crystal + MD structures) | Wilson 99% Confidence interval |
|---|---|---|---|---|
| Agonists/Antagonists | Random | 0.72 | 0.86 | (0.82, 0.88) |
| Agonists/Antagonists | Methadone | 0.84 | 0.99 | (0.82, 0.88) |
| Agonists/Antagonists | Fentanyl | 0.77 | 0.93 | (0.98, 1.0) |
| Expert curated dataset | Random | 0.73 | 0.85 | (0.67, 0.75) |
| Expert curated dataset | Methadone | 0.89 | 0.94 | (0.51, 0.59) |
| Expert curated dataset | Fentanyl | 0.81 | 0.91 | (0.88, 0.93) |

Example 5

Docking to both MD states and crystal structures statistically significantly improves ability over crystals alone to distinguish μOR binders from non-binders. Table below shows median ROC Area Under the Curve (AUC) performance over the validation set over 1,000 train-valid splits for different split and model types. Differences between crystal lone and crystal+MD structures methods are considered statistically significant if the lower bound of a 99% Wilson scoring confidence interval (CI) is greater than 0.5. Note that, for each dataset, incorporating MD-derived structures in addition to the crystal structures confers a statistically significant improvement in ability to distinguish binders from non-binder as measured by AUC. Notably, when molecules with similar scaffolds (as measured by a Tanimoto similarity score of ≥0.7) are removed from the training data, models remain able to distinguish binders from non-binders. This indicates that models fit in this way have the capacity to discover new opioid scaffolds in addition to derivatives of existing ones.

Datasets consist of compounds with experimentally known values of binding affinity to μOR. Datasets termed "Measured Ki" include only those compounds with a real-numbered Ki value; datasets termed "All" also include compounds that have no listed Ki but are termed "Not Active". Therefore, "Measured Ki" datasets are subsets of the "All" series of datasets. Binders are considered to be compounds with a pIC50 greater than some cutoff (listed in the "Dataset" table) and non-binders with a pIC50 lower than that same cutoff. For example, "All, pIC50 cutoff=7.0" indicates a dataset wherein (a) both ligands with a measurable pIC50<7.0 and those listed as "Not Active" are considered non-binders, and (b) both ligands with a measurable pIC50~7.0 and other known agonists and antagonists are considered to be binders.

| Dataset | Split | AUC (cyrstals alone) | AUC (Crystal + MD structures) | Wilson 99% Confidence interval |
|---|---|---|---|---|
| Measured pIC50, cutoff = 6.0 | Random | 0.59 | 0.64 | (0.76, 0.82) |
| Measured pIC50, cutoff = 7.0 | Random | 0.59 | 0.71 | (0.99, 1.0) |
| Measured pIC50, cutoff = 8.0 | Random | 0.58 | 0.74 | (0.99, 1.0) |
| All, pIC50, cutoff = 5.3 | Random | 0.78 | 0.87 | (0.99, 1.0) |
| All, pIC50, cutoff = 6.0 | Random | 0.73 | 0.82 | (0.99, 1.0) |
| All, pIC50, cutoff = 7.0 | Random | 0.67 | 0.78 | (0.99, 1.0) |
| All, pIC50, cutoff = 8.0 | Random | 0.65 | 0.79 | (0.99, 1.0) |
| All, pIC50, cutoff = 5.3 | Scaffold | 0.77 | 0.81 | (0.73, 0.80) |
| All, pIC50, cutoff = 6.0 | Scaffold | 0.78 | 0.83 | (0.73, 0.80) |
| All, pIC50, cutoff = 7.0 | Scaffold | 0.66 | 0.79 | (0.86, 0.91) |
| All, pIC50, cutoff = 8.0 | Scaffold | 0.64 | 0.78 | (0.85, 0.9) |

Example 6

Identification of Several Novel Opioid-Active Ligands, FMP4

The method entailed herein identified a novel ligand, FMP4. Notably, FMP4 lacks the hallmarks of synthetic opioids in that it does not have a basic tertiary amine or phenol.

A group of 133,564 small molecules were docked to both crystal structures and the computationally modeled conformers of μOR to yield a 133,564 row by 27 column feature matrix where entry (i,j) is the docking score of the i'th ligand to the j'th conformational state. The two trained random forest models for binding and agonism were applied to each library ligand, yielding a final score computed from the product of the two values:

$$P(binder \cap agonist|model) = P(binder|model_b) \cdot P(agonist|model_a)$$

The model performance and scaffolds of hits are highly sensitive to the pIC50 cutoff chosen for binary classifiers. While models with a lower affinity threshold for binding generally have a higher AUC, top hits have been shown to be biased toward compounds with a tertiary, basic nitrogen similar to known scaffolds. Random forest models with a pIC50 cutoff of 8.0 (10 nM) are used to optimize for novel scaffold discovery. In some embodiments, the pIC50 may be at least 3.0, 4.0, 5.0, 6.0, 7.0, 8.0, 9.0, 10.0, 11.0, or more. In some embodiments, the pIC50 may be from 3.0 to 11.0, 3.0 to 10.0, 3.0 to 9.0, 3.0 to 8.0, 3.0 to 7.0, 3.0 to 6.0, 3.0 to 5.0, 5.0 to 11.0, 5.0 to 10.0, 5.0 to 9.0, 5.0 to 8.0, 5.0 to 7.0, 8.0 to 11.0, or 8.0 to 10.0.

Thirty available, highest scoring compounds were experimentally assayed. At least three of the thirty exhibited micromolar affinity for μOR. One compound, FMP4, has a unique structure: no basic amine or phenol. In further binding assays in opioid transfected cell lines, FMP4 has a binding affinity of 3217±153 nM, 2503±523 nM, and 8143±1398 nM at MOR-1, KOR-1, and DOR-1 respectively. FMP4 is also a weak MOR-1 partial agonist in [35S]GTPγS functional assays. FMP4 is distinct from known opioid agonists and antagonists, with a maximum Tanimoto score of 0.44 compared to other known agonists and antagonists for the μOR. FMP4-like compounds in the same data set were characterized in binding assays and two compounds FMP1 and FMP16 show <10 μM affinity at MOR-1.

Figure 7:
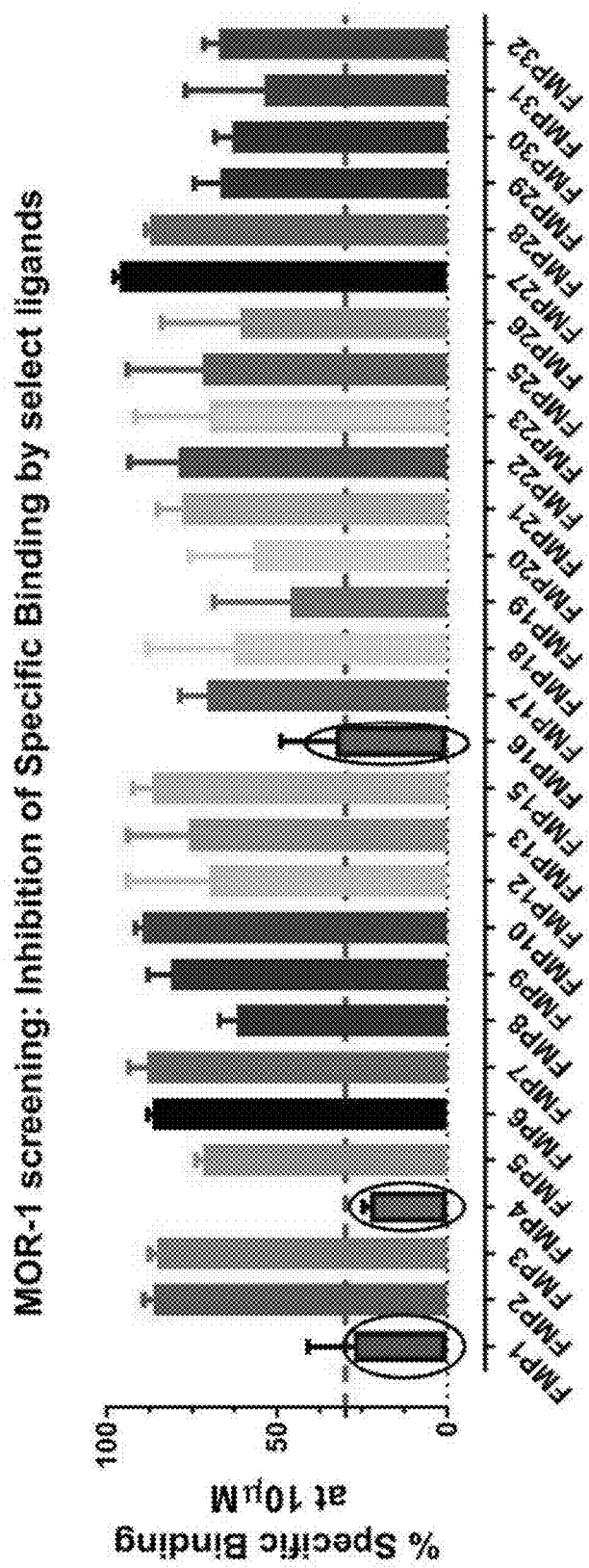
FIG. 7 illustrates an example of screening of MOR-1 binders in accordance with an embodiment of the invention.
Figure 8A:
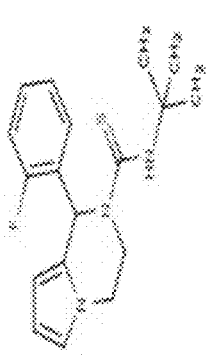
Figure 8A:
Figure 8A:
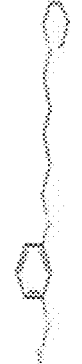
Figure 8A:
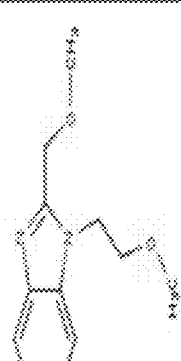
Figure 8A:
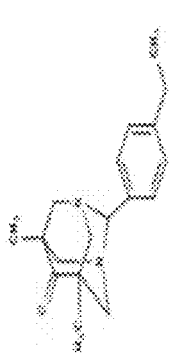
Figure 8A:
Figure 8A:
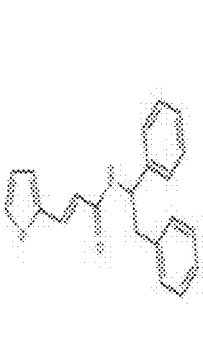
Figure 8A:
Figure 8C:
Figure 8C:
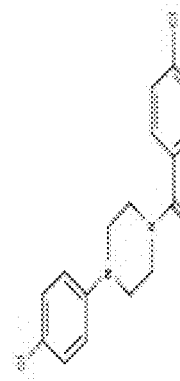
Figure 8C:
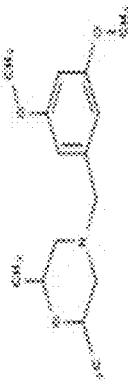
Figure 8C:
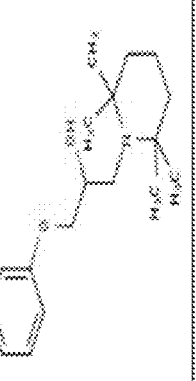
Figure 8C:
Figure 8C:
Figure 8C:
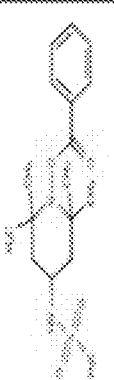
Figure 8C:
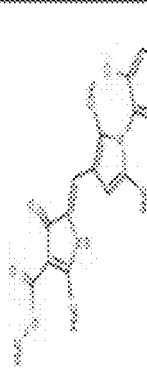

FIG. 7 shows screening of MOR-1 binders: Inhibition of 125 IBNtxA specific binding at MOR-1 was carried out at a single dose 10 μM concentration. Three compounds FMP1, 4 and 16 (circled) showed ~30% inhibition of MOR-1 binding (red dotted line represents compounds showing-30% inhibition). Each panel is a representative experiment that has been independently replicated at least three times. FIGS. 8A-8D illustrate structures and molecular weights for FMP1-FMP32.

Example 7

Analysis of FMP4 and Identification of a Novel Active-Like State of μOR

Modeling predicted that FMP4 binds to and facilitates activation of μOR in a unique way. FMP4 has a relatively high docking score for MD state 3 which is calculated to be important for agonism and binding. FIG. 1 shows that tIC.1, the slowest tICA reaction coordinate, connects the two crystallographic states. FIG. 2 shows that the second slowest tICA, tIC.2 is kinetically orthogonal to tIC.1 and defines several non-crystallographic states.

Measured by its progress along tIC.1 and by traditional metrics of GPCR literature such outward orientation of transmembrane helix 6 and bulged configuration of the NPxxY motif residues $N332^{7.48}$-$Y336^{7.53}$, MD state 3 is a novel active-like state of μOR. Near the orthosteric binding site, State 3 entails a rearrangement of $Q124^{2.60}$ $M151^{3.36}$, $H297^{6.52}$, $Y299^{6.54}$ and $W318^{6.35}$. The new positions of $M151^{3.36}$ and $H297^{6.52}$ enable FMP4 to occupy a pose that would be sterically forbidden in the active crystal structure as seen in FIG. 1. In contrast to the co-crystallized agonist, FMP4 engages in a π-T interaction with $W293^{6.48}$, a residue critical in gating μOR activation, and a hydrogen bond with $H297^{6.52}$.

Figure 9:
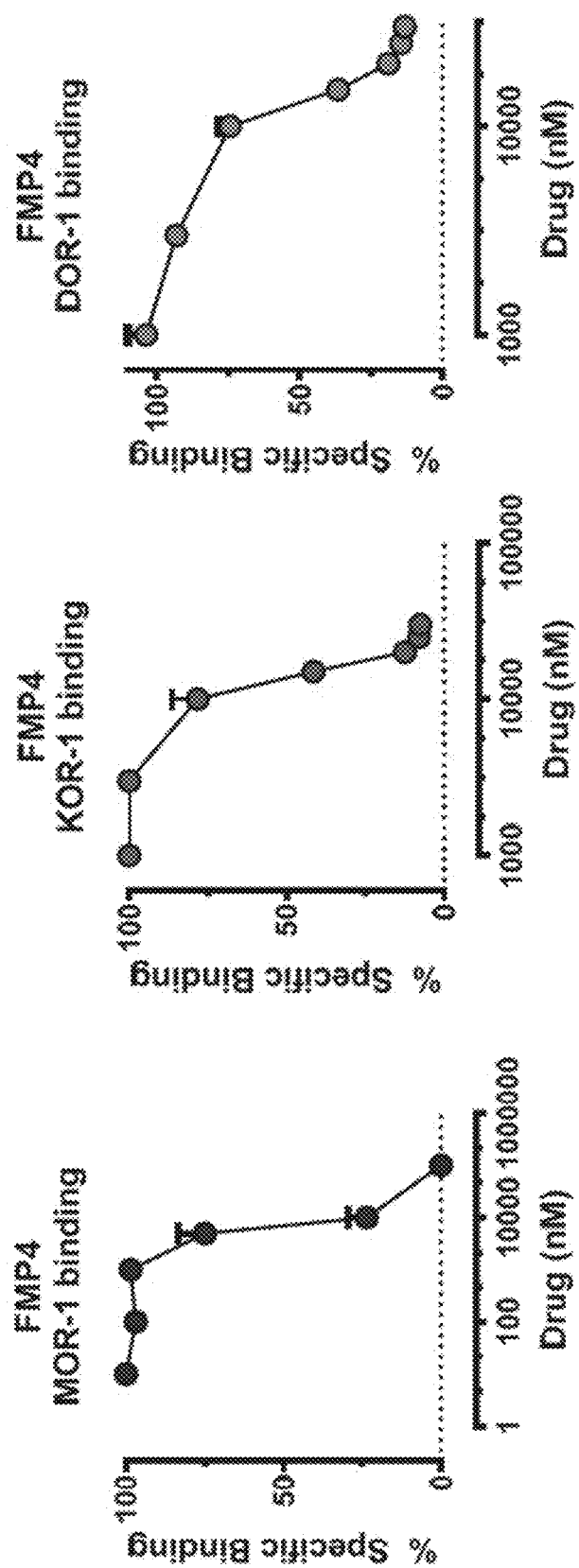
FIG. 9 illustrates competition studies with FMP4 against 125 I-IBNtxA (0.1 nM) in membranes from CHO cells in accordance with an embodiment of the invention.

FIG. 9 shows competition studies were performed with FMP4 against 125 I-IBNtxA (0.1 nM) in membranes from CHO cells stably expressing the indicated cloned mouse opioid receptors Each figure is a representative experiment that has been independently replicated at least three times. Error bars represent the SEM of triplicate samples. Error bars that cannot be seen are smaller than the size of the symbol. FMP4 had 3217±153 nM, 2503±523 nM and 8143±1398 nM affinity at MOR-1, KOR-1 and DOR-1 respectively.

What is claimed is:

1. A method performed by one or more computers for predicting a relationship between a ligand and a receptor, the method comprising:
    identifying a plurality of clustered conformations of the receptor, comprising:
        performing a simulation of molecular dynamics of the receptor over a time interval, wherein the simulation defines a collection of simulated conformations of the receptor; and
        clustering the collection of simulated conformations of the receptor to generate the plurality of clustered conformations of the receptor;
    computing, for each of the plurality of clustered conformations of the receptor, a respective docking score between the clustered conformation of the receptor and the ligand; and
    receiving, by a machine learning model, a model input to the machine learning model that comprises the respective docking score for each of the plurality of clustered conformations of the receptor,
    wherein the machine learning model is parameterized by a set of machine learning model parameters that have been trained by a supervised machine learning technique;
    processing the model input that comprises the respective docking score for each of the plurality of clustered conformations of the receptor using the machine learning model, in accordance with trained values of the set of machine learning model parameters, to generate a model output of the machine learning model that comprises a binding score,
    wherein the binding score is a score that characterizes a binding affinity of the ligand for the receptor.

2. The method of claim 1, wherein the collection of simulated conformations of the receptor comprises at least one non-crystallographic state.

3. The method of claim 1, wherein performing the simulation of the molecular dynamics of the receptor comprises simulating an interaction of the receptor with the ligand.

4. The method of claim 1, wherein clustering the collection of simulated conformations of the receptor comprises performing a dimensionality reduction operation on the collection of simulated conformations of the receptor.

5. The method of claim 1, wherein for each of the plurality of clustered conformations of the receptor, computing the docking score between the clustered conformation of the receptor and the ligand comprises:
    simulating a docking of the ligand and the clustered conformation of the receptor.

6. The method of claim 1, wherein the machine learning model comprises one or more random forest models.

7. The method of claim 1, further comprising physically testing reactions of the ligand with the receptor.

8. The method of claim 1, wherein the machine learning model comprises a neural network model.

9. The method of claim 1, wherein the model output of the machine learning model further comprises an agonist score that characterizes a likelihood that the ligand is an agonist for the receptor.

10. The method of claim 1, wherein the model output of the machine learning model comprises: (i) the binding score that characterizes the binding affinity of the ligand for the receptor, and (ii) an agonist score that characterizes a likelihood that the ligand is an agonist for the receptor; and
wherein the method further comprises:
generating an overall score by combining the binding score and the agonist score.

11. The method of claim 10, wherein generating the overall score by combining the binding score and the agonist score comprises:
computing a product of the binding score and the agonist score.

12. The method of claim 1, wherein the time interval of the molecular dynamics simulation has a duration of at least one millisecond.

13. The method of claim 1, wherein clustering the collection of simulated conformations of the receptor comprises:
applying k-means clustering to the collection of simulated conformations of the receptor.

14. The method of claim 1, wherein the collection of simulated conformations of the receptor comprises at least 100,000 simulated conformations of the receptor.

15. The method of claim 1, wherein clustering the collection of simulated conformations of the receptor comprises:
generating a set of clusters, wherein a number of clusters in the set of clusters is less than a number of simulated conformations of the receptor in the collection of simulated conformations of the receptor.

16. One or more non-transitory computer storage media storing instructions that when executed by one or more computers cause the one or more computers to perform operations for predicting a relationship between a ligand and a receptor, the operations comprising:
identifying a plurality of clustered conformations of the receptor, comprising:
performing a simulation of molecular dynamics of the receptor over a time interval, wherein the simulation defines a collection of simulated conformations of the receptor; and
clustering the collection of simulated conformations of the receptor to generate the plurality of clustered conformations of the receptor;
computing, for each of the plurality of clustered conformations of the receptor, a respective docking score between the clustered conformation of the receptor and the ligand; and
receiving, by a machine learning model, a model input to the machine learning model that comprises the respective docking score for each of the plurality of clustered conformations of the receptor,
wherein the machine learning model is parameterized by a set of machine learning model parameters that have been trained by a supervised machine learning technique;
processing the model input that comprises the respective docking score for each of the plurality of clustered conformations of the receptor using the machine learning model, in accordance with trained values of the set of machine learning model parameters, to generate a model output of the machine learning model that comprises a binding score,
wherein the binding score is a score that characterizes a binding affinity of the ligand for the receptor.

17. A system comprising:
one or more computers; and
one or more storage devices communicatively coupled to the one or more computers, wherein the one or more storage devices store instructions that, when executed by the one or more computers, cause the one or more computers to perform operations for predicting a relationship between a ligand and a receptor, the operations comprising:
identifying a plurality of clustered conformations of the receptor, comprising:
performing a simulation of molecular dynamics of the receptor over a time interval, wherein the simulation defines a collection of simulated conformations of the receptor; and
clustering the collection of simulated conformations of the receptor to generate the plurality of clustered conformations of the receptor;
computing, for each of the plurality of clustered conformations of the receptor, a respective docking score between the clustered conformation of the receptor and the ligand; and
receiving, by a machine learning model, a model input to the machine learning model that comprises the respective docking score for each of the plurality of clustered conformations of the receptor,
wherein the machine learning model is parameterized by a set of machine learning model parameters that have been trained by a supervised machine learning technique;
processing the model input that comprises the respective docking score for each of the plurality of clustered conformations of the receptor using the machine learning model, in accordance with trained values of the set of machine learning model parameters, to generate a model output of the machine learning model that comprises a binding score,
wherein the binding score is a score that characterizes a binding affinity of the ligand for the receptor.

18. The system of claim 17, wherein the collection of simulated conformations of the receptor comprises at least one non-crystallographic state.

19. The system of claim 17, wherein performing the simulation of the molecular dynamics of the receptor comprises simulating an interaction of the receptor with the ligand.

20. The system of claim 17, wherein clustering the collection of simulated conformations of the receptor comprises performing a dimensionality reduction operation on the collection of simulated conformations of the receptor.

* * * * *